(12) United States Patent  
Feng

(10) Patent No.: US 10,625,092 B2  
(45) Date of Patent: Apr. 21, 2020

(54) MAGNETIC DEVICES

(71) Applicant: Yvonne Ya-Wen Feng, Vancouver (CA)

(72) Inventor: Yvonne Ya-Wen Feng, Vancouver (CA)

(*) Notice: Subject to any disclaimer, the term of this patent is extended or adjusted under 35 U.S.C. 154(b) by 246 days.

(21) Appl. No.: 15/939,317

(22) Filed: Mar. 29, 2018

(65) Prior Publication Data

US 2018/0214709 A1  Aug. 2, 2018

Related U.S. Application Data

(62) Division of application No. 14/540,893, filed on Nov. 13, 2014, now Pat. No. 9,962,554.

(51) Int. Cl.
| | |
|---|---|
| *A61N 2/06* | (2006.01) |
| *A61H 23/06* | (2006.01) |
| *A61N 2/02* | (2006.01) |
| *A61N 2/00* | (2006.01) |

(52) U.S. Cl.
CPC ............. *A61N 2/06* (2013.01); *A61H 23/06* (2013.01); *A61N 2/006* (2013.01); *A61N 2/008* (2013.01); *A61N 2/02* (2013.01)

(58) Field of Classification Search
CPC .............. A61N 2/00–12; A61H 39/04; A61H 2201/10; A61H 23/006; A61H 23/06
See application file for complete search history.

(56) References Cited

U.S. PATENT DOCUMENTS

| | | | | |
|---|---|---|---|---|
| 4,231,137 A | * | 11/1980 | Fujimoto | A44C 5/2071 24/303 |
| 5,782,858 A | * | 7/1998 | Cheng | A61N 2/06 606/189 |
| 6,858,036 B1 | * | 2/2005 | Kim | A61H 39/04 606/189 |
| 10,293,175 B2 | * | 5/2019 | Watterson | A61N 2/06 |
| 2008/0319358 A1 | * | 12/2008 | Lai | A61H 39/04 601/134 |

* cited by examiner

*Primary Examiner* — Catherine B Kuhlman  
(74) *Attorney, Agent, or Firm* — Bayramoglu Law Offices LLC

(57) ABSTRACT

A device for non-invasive treatment of a disorder in a patient comprising a magnetic portion having a first side and a second side, a first metal portion having a first end and a second end, and a second metal portion configured for hand holding and having a first side and a second side, wherein second side of the second metal portion: (i) is coupled to the first side of the magnetic portion; and (ii) has a surface area that is less than the surface area of the first side of the magnetic portion; and wherein the first metal portion is coupled to the second side of the magnetic portion. The first metal portion is optionally fitted with a head. The disclosure further relates to non-invasive methods for treating a disorder in a patient, wherein said methods use said magnetic device.

13 Claims, 14 Drawing Sheets

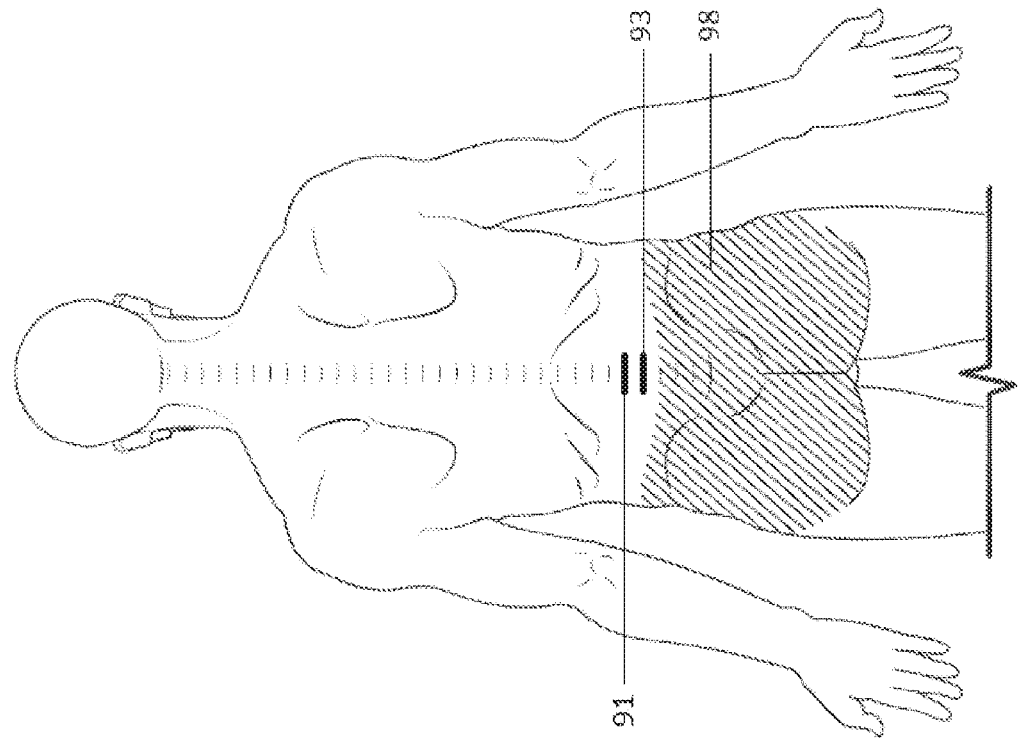
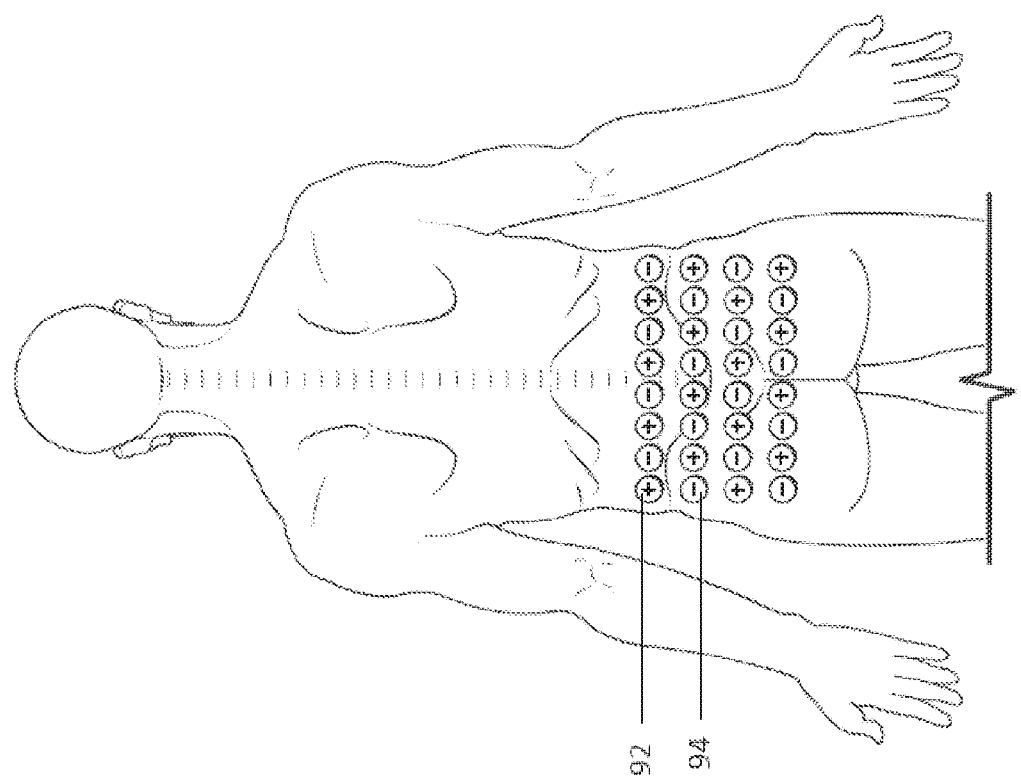

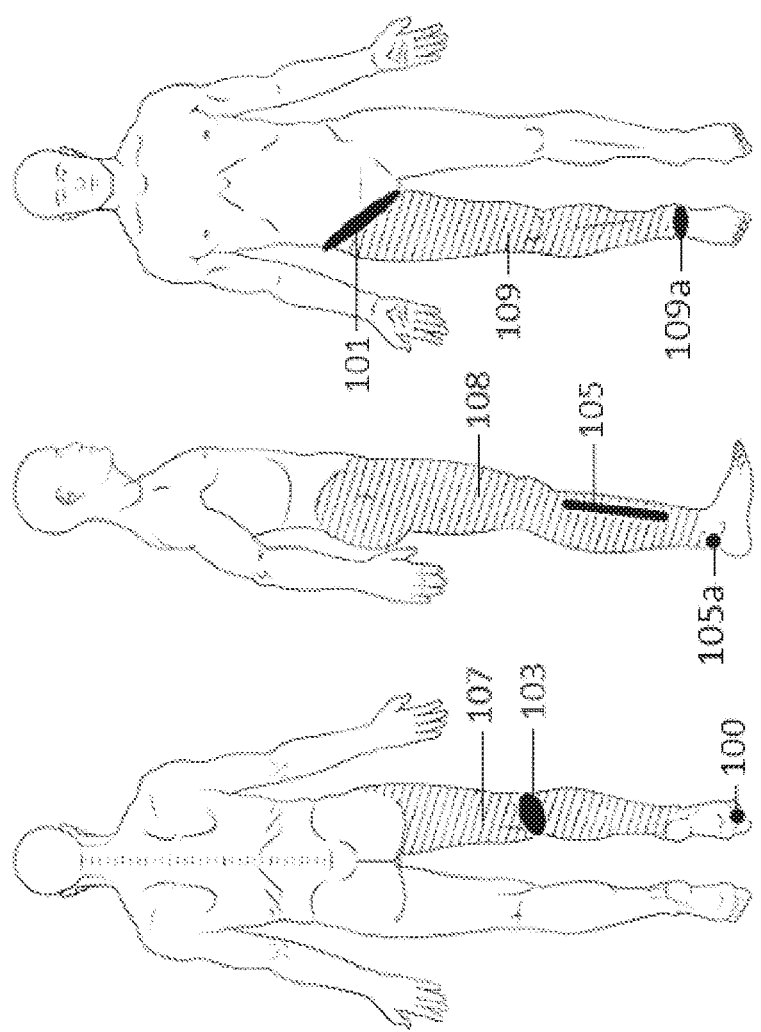

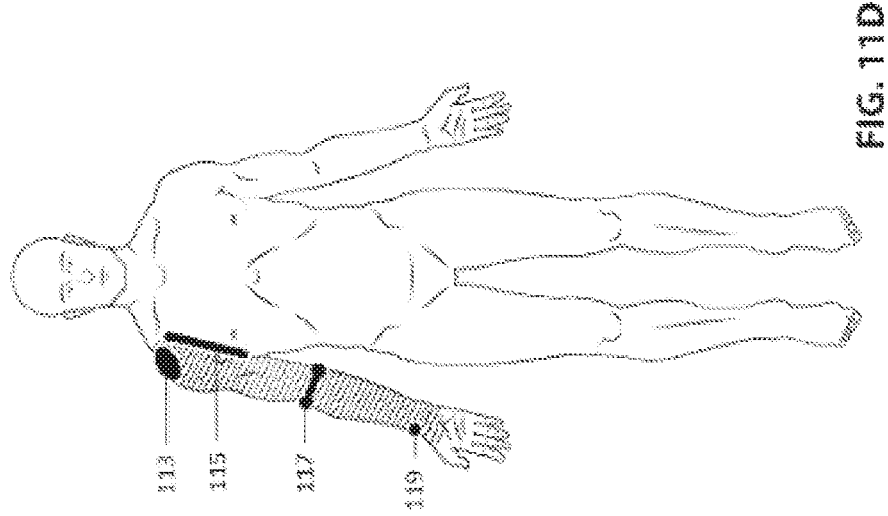
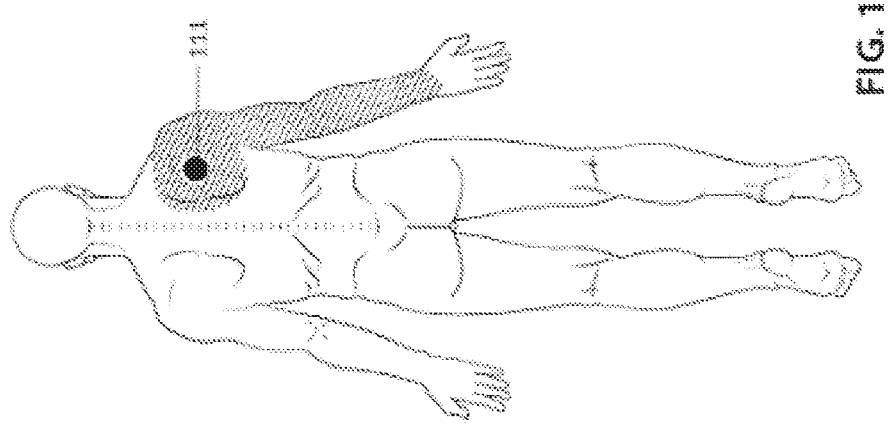

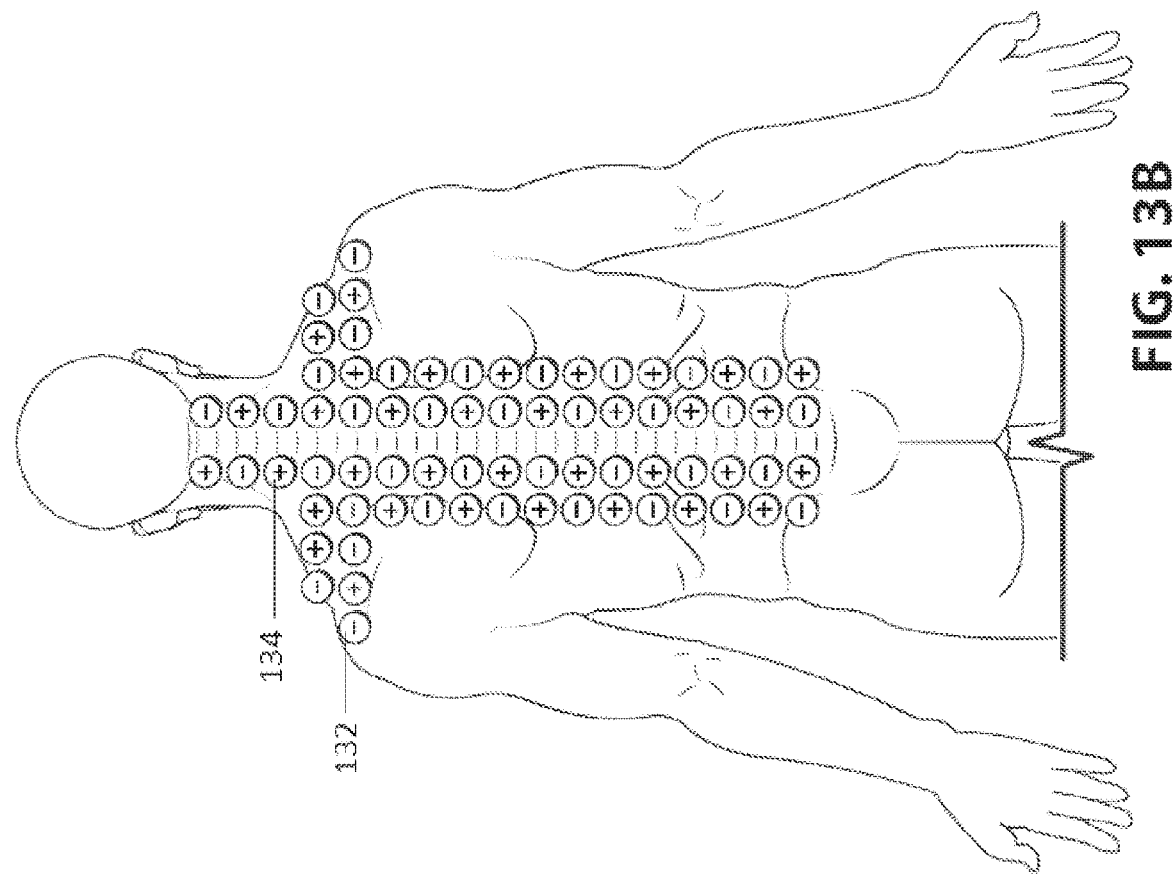
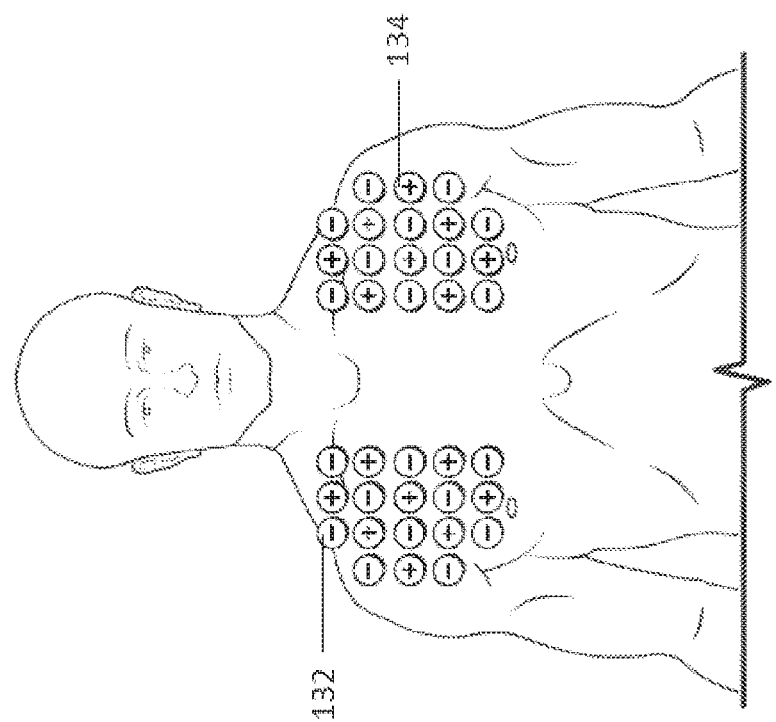

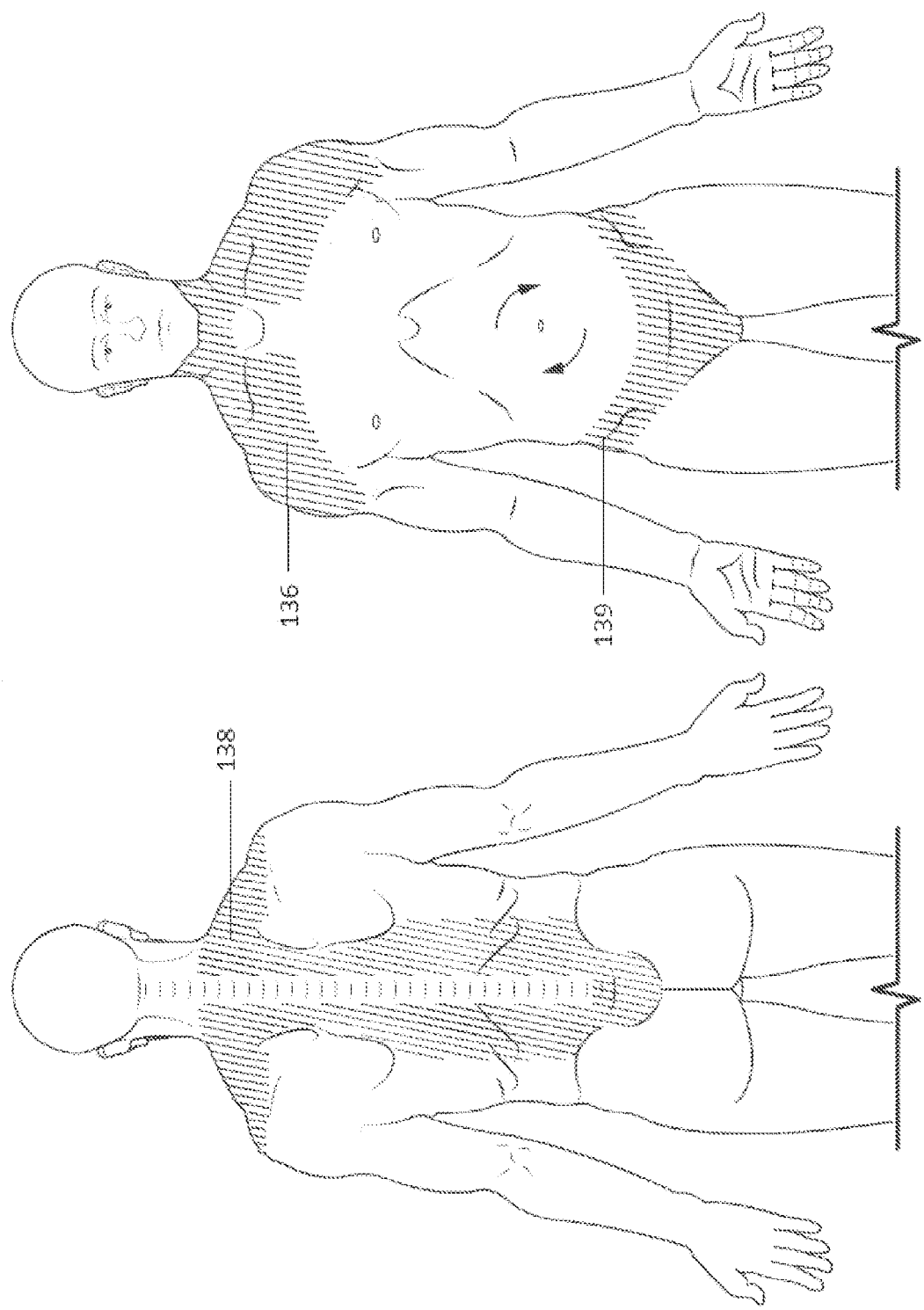

MAGNETIC DEVICES

CROSS-REFERENCE TO RELATED APPLICATION

This application is a divisional application of U.S. application Ser. No. 14/540,893 filed on Nov. 13, 2014, which is a continuation-in-part application of U.S. application Ser. No. 13/732,839, filed Jan. 2, 2013, which claims priority to U.S. application No. 61/646,705, filed on May 14, 2012. The disclosures of each are incorporated herein in their entireties.

BACKGROUND

This disclosure relates at least in part to a magnetic device and methods of using the magnetic device for treating disorders and diseases in the human body.

It is well known and acknowledged that modern medicine based on chemistry or biology or radiation often comes with undesirable and sometimes serious side effects. For certain disorders, such modern medicine is sometimes limited in its effectiveness, and is only able to control or slow the progression of the disorder. In such instances, modern medicine is not a long-term or ultimate solution. Furthermore, as human bodies develop along with the development of medicines based on chemistry or biology or radiation, human bodies may also develop immunity to these medicines, thus requiring further advances to the medicines themselves. As such, some patients choose to turn to traditional Eastern medical treatment techniques Which include, among others, traditional acupuncture, chiropractic, physiotherapy, massage therapy.

These traditional Eastern medical treatment techniques also have their shortcomings. For example, they may require frequent doctor visits, may be invasive (e.g. acupuncture), and may be limited in effectiveness. In many cases, Eastern medical treatment techniques have no influence on a patient if the underlying conditions are too severe, such as those resulting from major injuries suffered from major accidents.

Chiropractice is the use of manual power to manipulate mis-aligned spine discs back into alignment. This action can be dangerous, and may also cause partial or total paralysis of the body if performed improperly. In some cases, the dislocated or otherwise abnormal spine discs are so mis-aligned that it is impossible to safely perform a chiropractic manipulation. Even after the discs have been properly manipulated, chiropractice may still not be a long term solution given that the discs will generally continue to slip out of alignment. Chiropractice does not stabilize the spinal discs in their proper alignment permanently. In addition, if the disc is pushed back into alignment repeatedly, the disc may become arthritic.

Physiotherapy may have some ameliorative effects, mostly resulting from manipulating tendons and ligaments, and managing or easing pain by storing inflammation into different areas of the body. Repeated physiotherapy sessions are usually required before such ameliorative effects are experienced. Exercises are also good for rehabilitation, but do not cure the problem or provide a permanent solution to the problem. Similarly, massage therapy, which entails manipulating muscles, is good for short-term prevention and relief of tension, but does not provide long-term solution. For example, massage therapy does not have the power to ameliorate any serious damage or condition.

Thus, alternative methods of treating diseases or disorders in a time-effective and cost-effective manner are desired.

SUMMARY

In an aspect of the disclosure, there is a device for non-invasive treatment of a physical disorder or disease in a patient, the device comprising: (i) a magnetic portion, wherein the magnetic portion has a first side and an opposite second side; (ii) a first metal portion, wherein the first metal portion has a first end and a second end; and (iii) an second metal portion configured for hand holding, wherein the second metal portion has a first side and a second side; wherein the second side of the second metal portion: (i) is coupled to the first side of the magnetic portion; and (ii) has a surface area that is less than the surface area of the first side of the magnetic portion; and wherein the first end of the first metal portion is coupled to the second side of the magnetic portion. The magnetic portion may be a permanent magnet or an electromagnet. The size of the magnetic field in the electromagnet may be increased or decreased according to the needs of the patient and/or the severity of the treated condition. The metal portions may be made of any suitable metal (e.g. steel).

In an aspect of the disclosure, there is a non-invasive method for treating a disorder in a patient, the method comprising: (i) applying a plurality of magnetic suction cups to one or more treatment areas on the patient; and (ii) using the magnetic device over the one or more treatment areas, whereby the head or the second end of the lower metal portion contacts the treatment area.

This summary does not necessarily describe the entire scope of all aspects of the disclosure. Other aspects, features and advantages will be apparent to those of ordinary skill in the art upon review of the following description of specific embodiments.

BRIEF DESCRIPTION OF THE DRAWING

In the accompanying drawings, which illustrate one or more exemplary embodiments of the disclosure:

FIG. 9A is a back elevation view of a human body showing the placement of magnetic suction cups on the lower back and buttocks region of the human body, for the treatment of the sciatic nerve.

FIG. 9B is a back elevation view of a human body showing the lower back and buttocks region of the human body for the treatment of disorders of the sciatic nerve.

FIG. 10C is a back elevation view of legs of a human body showing the hamstring and calf regions of a right leg of the human body, for the treatment of disorders in the right leg.

FIG. 10D is a side elevation view of a right leg of a human body showing the leg region of the right leg, for the treatment of disorders in the right leg.

FIG. 10E is a front elevation view of legs of a human body showing the quadriceps and shinbone regions of a right leg of the human body, for the treatment of disorders in the right leg.

FIG. 11C is a back elevation view of a human body showing the right scapula and right upper arm regions of the human body, for the treatment of disorders in the right arm.

FIG. 1D is a front elevation view of a human body showing the right arm region of the human body, for the treatment of disorders in the right arm.

FIG. 13A is a front elevation view of a human body showing the placement of magnetic suction cups on the right and left pectoral regions of the human body, for the treatment of the body trunk.

FIG. 13B is a back elevation view of a human body showing the placement of magnetic suction cups on the neck, shoulder and back regions of the human body, for the treatment of the body trunk.

FIG. 13C is a back elevation view of a human body showing the neck, shoulder and back regions of the human body, for the treatment of the body trunk.

FIG. 13D is a front elevation view of a human body showing the neck, pectoral and groin regions of the human body, for the treatment of the body trunk.

DETAILED DESCRIPTION

Figure 1:
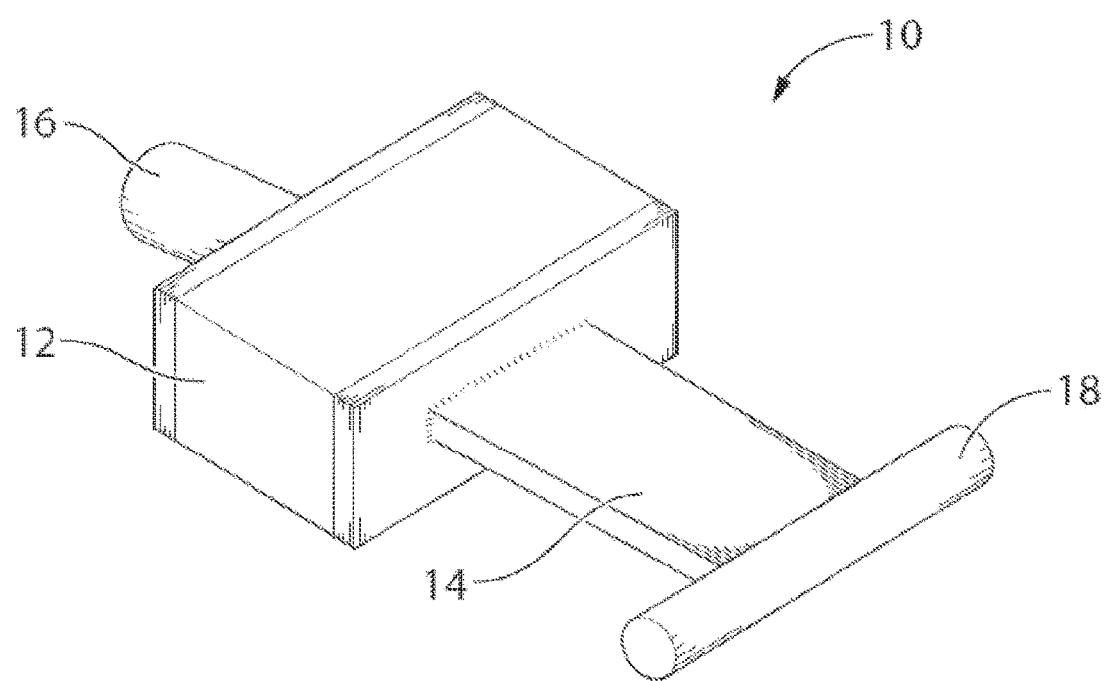
FIG. 1 is a perspective view of a magnetic device according to an embodiment, wherein the embodiment comprises a second metal portion, a magnetic portion, a first metal portion, and a head connected to the first metal portion.

Directional terms such as "top", "bottom", "upwards", "downwards", "vertically", and "laterally" are used in the following description for the purpose of providing relative reference only, and are not intended to suggest any limitations on how any article is to be positioned during use, or to be mounted in an assembly or relative to an environment. Reference to a magnetic device in the description includes a permanent magnetic device and/or an electro-magnetic device. Numbered dark spots or lines in the Figures indicate areas that require longer, repeated and more intensive treatment.

The teachings of this disclosure relate to the treatment of disorders and/or diseases. The disclosure is related to the field of organic green medicine and does not necessarily need to be supplemented by any natural or synthetic supplements or medicine. In addition, the teachings of this disclosure have no significant side effects, are non-invasive, do not involve chemicals, and do not produce major waste or require recycling. The teachings of this disclosure are based on many years of research and exploration for better ways of treating disorders and/or diseases in a human patient.

In an aspect of this disclosure, there is a device for treating disorders and diseases in a patient, the device being capable of delivering powerful magnetic signals into the patient (e.g., possible delivery of magnetic signals into the patient s blood which circulates in the patient's body). The device comprises a second metal portion, a magnetic portion, and a first metal portion. The second metal portion is connected to the magnetic portion at one pole of the magnetic portion, and the first metal portion is connected to the magnetic portion at the opposite pole of the magnetic portion. Such device may be configurable to fit the body contours of the patient. Through such device, pressure may be exerted on the skin of the patient that overlies a targeted tissue or organ. The magnetic device may be designed in different shapes and sizes, and possess different magnetic field strengths, as per the requirements of the patient and severity of the disorder and/or disease. The magnetic device may comprise a permanent magnet or an electromagnet. The size of the magnetic field emitted by the electromagnet may be increased or decreased according to the needs of the patient and/or the severity of the treated condition. The metal portions may be made of any suitable metal (e.g. steel).

In an aspect of the disclosure, there are non-invasive methods of treating disorders and/or diseases in the body of a patient. The methods of treatment involve using a magnetic device in combination with: (i) a plurality of magnetic suction cups; and (ii) techniques such as acupuncture, chiropractic, massage, and physiotherapy.

Without the need to apply large forces, the treatment methods disclosed herein may be used to re-align dislocated spinal discs, thereby releasing pressure from the spinal discs, removing damaged tissues and bacteria from the spinal discs, and allowing the spinal discs to gain space and naturally heal. For example, bulging or herniated discs may be treated and cured instantly. While not wishing to be bound by theory, the magnetic device and treatment methods can break down damaged tissues surrounding abnormal spinal discs and may kill bacteria contained therein. The toxins (including killed bacteria) can then be released from the cartilage in the spinal discs' joints, thereby allowing the cartilage to rejuvenate, and joints to loosen. Once the discs have loosened, the dislocated or abnormal (e.g., wounded or injured) discs can shift back into alignment as the body moves, and the disc may start to heal after the gap seals between the spinal vertebrae. The patient may experience a strong "click" or shock in the back after a few days or weeks. The "click" or shock indicates that the spinal cord or previously abnormal spinal discs have healed. Through the use of the magnetic device and the treatment methods disclosed herein, patient disorders may be permanently fixed.

The treatment methods also effectively improve the patient's internal systems including, but not limited to, organs of the patient, particularly since the spinal discs directly or indirectly control the nerves in other parts of the body. Disorders in the lung, stomach, liver, throat, digestive system, and large intestine may be treated to different degrees by the magnetic device and treatment methods disclosed herein.

The magnetic device and treatment methods can be particularly effective in treating disorders related to brain and central nervous system. They may, for example, be used in combination with a plurality of magnetic suction cups and treatment methods intended for treating the same disorders. For example, it is believed that the teachings disclosed herein can break down blood clots, and clear toxins and unwanted chemicals in the occipital area where blood circulation is blocked to the brain. Blood flow to the brain can be unblocked and blood is able to flow fluidly. Repeated use of the magnetic device can stimulate and excite the nerves in the brain and/or rejuvenates weakened or damaged nerves and tissues. Many conditions or disorders, such as insomnia, anxiety, migraine, pending aneurysms, concussions and depression can be treated instantly by the magnetic device and treatment methods.

The magnetic device and treatment methods may also cause toxins (such as harmful chemicals or inflammation) in damaged tissue or dysfunctional internal organs (e.g., sweat gland) in a human body to leave the body, thus allowing the damaged tissue or dysfunctional internal organ to regain function and heal, instead of allowing all toxins and inflammation to be stored in different areas and postpone the problems, and thereby complicating or worsening the conditions or disorders. Examples of tissues or organs include shoulder, knee, hip, ankle, foot, elbow, arm, hand, joint, and wrist.

Embodiments of the present teachings have proved to be very effective, and provided surprisingly good results and possible cures in a very short period of time in most cases, or even instantly in some cases. The teachings of this disclosure are expected to provide an alternative to most (e.g., 50-60%), if not all, of the Eastern medicine techniques. The magnetic device and the treatment methods can be used to treat both emergency medical cases and non-emergency disorders, such as chronic pains and illness. The magnetic device and treatment methods disclosed herein may also serve as preventive measures (e.g. by reducing inflammation).

The magnetic device and the treatment methods disclosed herein may have ameliorative effects on patients suffering from Parkinson's disease, multiple sclerosis, paralysis, lupus, amyotrophic lateral sclerosis, scoliosis, fibromyalgia, diabetes, meningitis, hi-polar disorder, chronic traumatic encephalopathy, chronic fatigue syndrome, spinal diseases and disorders, insomnia, anxiety, migraines, dementia, eating disorders, the imminent occurrence of aneurysms, eye disorders, depression, concussions, meningitis, epilepsy, sciatica, sinus, hay fever, temporomandibular joint disorders, and tinnitus, pneumonia, compressed discs, bulging discs, herniated discs, degenerative discs, thinning discs, speech disorders, ADHD, panic attacks, post-traumatic stress disorder, comas, or vegetative states. It is also believed that the treatment method disclosed herein can prevent disorders and/or diseases that develop into blockages in arteries which may lead to heart attacks, or cause kidney stones, kidney failure, pancreatic dysfunction, precursor diseases to breast and prostate cancers. The magnetic device and the treatment methods may also treat small and mild ailments such as scar tissues, unhealed muscles, numbness, fingers, toes, joint arthritis, and mild cases of fevers, colds or coughs, instantly.

Magnetic Device

In an aspect of the disclosure, and according to an embodiment of this aspect, there is shown in FIG. 1 a device 10 for the treatment of a physical disorder or disease in a body of a patient. Device 10 comprises a second metal portion 16, a magnetic portion 12, a first metal portion 14, and a head 18 that is coupled to the first metal portion 14.

Magnetic portion 12 comprises an electromagnet or permanent magnet. The strength of the magnet is proportional to the size of the magnet. Permanent magnetic portion may be made of a neodymium-iron-boron composition. The neodymium-iron-boron composition may possess the chemical formula $Nd_2Fe_{14}B$, may have a material grade of N40, and may have a material residual flux density of 1.28 Tesla. Magnetic portion 12 comprises: (i) a first side to which second metal portion 16 is coupled; and (ii) a second side to which first metal portion 14 is coupled. The first side and second side of the magnetic portion 12 are substantially flat and even. As depicted in FIG. 1, the magnetic portion 12 is in the shape of a rectangular prism. However, as depicted in other exemplar)/embodiments shown in FIGS. 2 to 6, the magnetic portion may be of different shapes.

Second metal portion 16 is configured for hand-holding. In FIG. 1, second metal portion 16 is depicted as having a cylindrical shape. However, the second metal portion may be of different shapes in alternative embodiments. Second metal portion 16 comprises: (i) a first side that faces away from magnetic portion 12; and (ii) a second side that faces and is coupled to the first side of magnetic portion 12. The first side and the second side of second metal portion 16 can be substantially flat and even. As depicted in FIG. 1, second metal portion 16 is integrally coupled to magnetic portion 12. However, second metal portion 16 may be detachably or releasably coupled to magnetic portion 12.

In the embodiment shown in FIG. 1, the second side of second metal portion 16 has a surface area that is less than the surface area of the first side of the magnetic portion 12. More specifically, the diameter of the second side of second metal portion 16 is less than the width and length of the first side of magnetic portion 12. In the embodiment shown in FIG. 1, second metal portion 16 also occupies a volume that is less than the volume occupied by magnetic portion 12.

The difference in volume between second metal portion 16 and magnetic portion 12 (and/or surface area between the second side of second component 16 and the first side of magnetic portion 12) allows an operator of device 10 to assume various hand grip positions on device 10. For instance, the operator may hold second metal portion 16 as he would a pen. In doing so, he may choose to rest the side of his palm on the first side of magnetic portion 12, thereby relieving stress in his hand. Alternatively, the operator may choose to grip the second metal portion in a manner such that the first side of second metal portion 16 faces the operator's palm. In doing so, at least two of the operator's knuckles would rest on the first side of magnetic portion 12, thereby relieving stress in the operator's hand and providing the operator with the option of applying force on a particular body area of the patient that is in contact with head 18 of device 10. Such differences also allow the operator of device 10 to: (i) control and manipulate the angle at which the magnetic field emitted from magnetic portion 12; (ii) control and manipulate how device 10 interacts with the body of the patient; and/or (iii) prolong the onset of fatigue in the operator's hand or arm. This is important considering that the methods of treatment described later in this disclosure, which involve the use of the magnetic device, may last upwards of 20 minutes or even longer.

First metal portion 14 comprises: (i) a first end that is coupled to magnetic portion 12 at the second side of magnetic portion 12; and (ii) a second end that terminates at head 18. The first end of first metal portion 14 is substantially flat and even. First metal portion 14 may be integrally, detachably or releasably coupled to magnetic portion 12 and head 18. First metal portion 14 also comprises a length. Different severities of disorders will call for differences in distances between magnetic portion 12 and the body of the patient. As such, and depending on the severity of the disorder that is treated, the length of first metal portion 14 may vary.

Head 18 is coupled to first metal portion 14, and is constructed of metal. Preferably but not necessarily, head 18 and first metal portion 14 are constructed of the same metal. As depicted in FIG. 1, head 18 is integrally coupled with first metal portion 14 at first metal portion 14's second end. However, head 18 may be detachably or releasably coupled to first metal portion 14 in alternative embodiments. As depicted in FIG. 1, head 18 has a long cylindrical shape, wherein the length of head 18 is not parallel (e.g. perpendicular) to the length of first metal portion 14. However, and as depicted in other exemplary embodiments shown in FIGS. 2-6, the head may be of other shapes. The head may be configured to match the contours of the body of the patient, particularly to the body areas of the patient that require treatment. The shape and size of the head also depends on the particular area of the patient that requires treatment.

Figure 2:
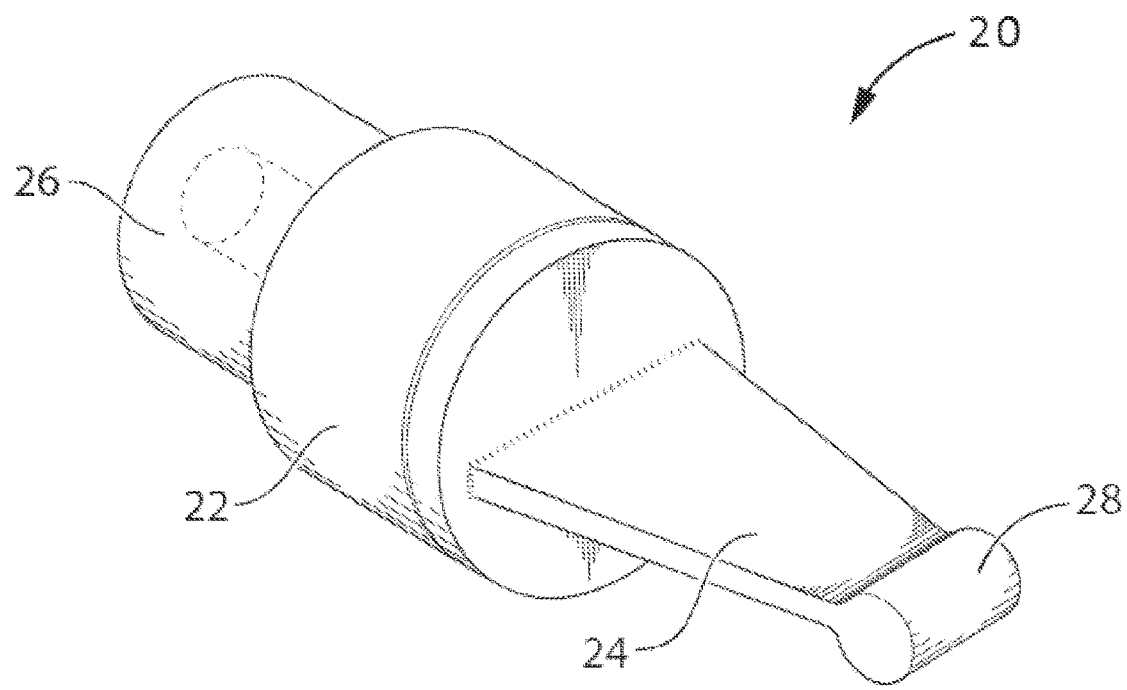
FIG. 2 is a perspective view of a magnetic device according to another embodiment, wherein the embodiment comprises a second metal portion, a magnetic portion, a first metal portion, and a head connected to the first metal portion.

Referring to FIG. 2 and according to an embodiment, there is a device 20 comprising a magnetic portion 22 that has a cylindrical shape, wherein the magnetic portion 22 comprises: (i) a first side that is coupled to a cylindrical second metal portion 26, the second metal portion 26 being hollow at its core; and (ii) a second side that is coupled to a first metal portion 24. First metal portion 24 is wedge-shaped and comprises a first end that is coupled to magnetic portion 22 and a second end that terminates in a cylindrical head 28. The length of cylindrical head 28 is approximately equal to the width of the second end of first metal portion 24. First metal portion 24 and head 28 depicted in FIG. 2 allows the user of magnetic device 20 to apply greater pressure on body areas of the patient that require treatment.

Figure 3:
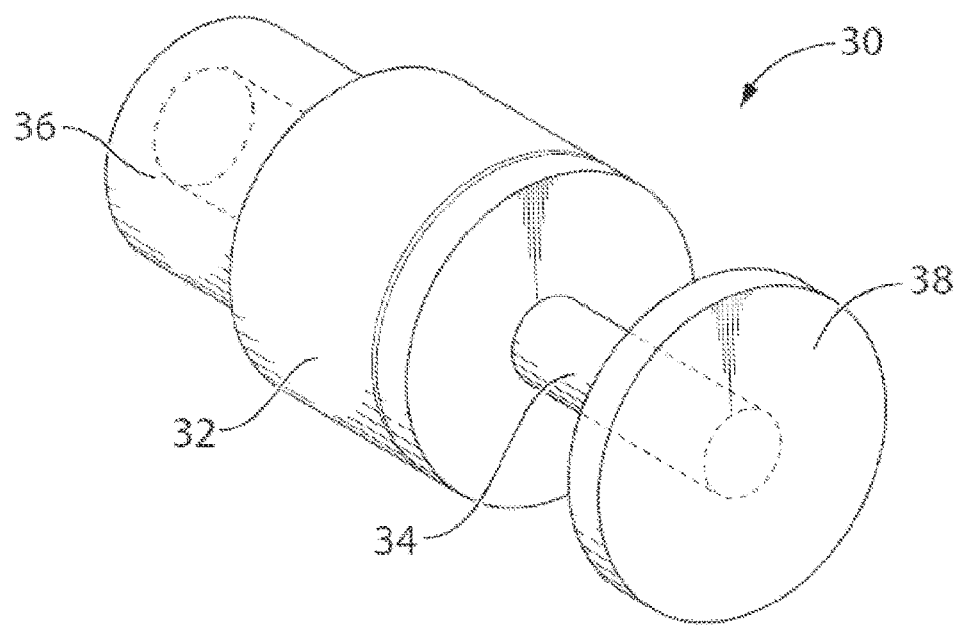
FIG. 3 is a perspective view of a magnetic device according to another embodiment, wherein the embodiment comprises a second metal portion, a magnetic portion, a first metal portion, and a head connected to the first metal portion.

Referring to FIG. 3 and according to an embodiment, there is a magnetic device 30 comprising a cylindrical second metal portion 36, the second metal portion 36 being hollow at its core, a cylindrical magnetic portion 32, a cylindrical first metal portion 34, and a head 38 that is in a shape of a disc. The disc-shaped head allows the magnetic field emitted from magnetic portion 32 to interact with an area of the patient's body that is defined by the area of disc-shaped head 38.

Figure 4:
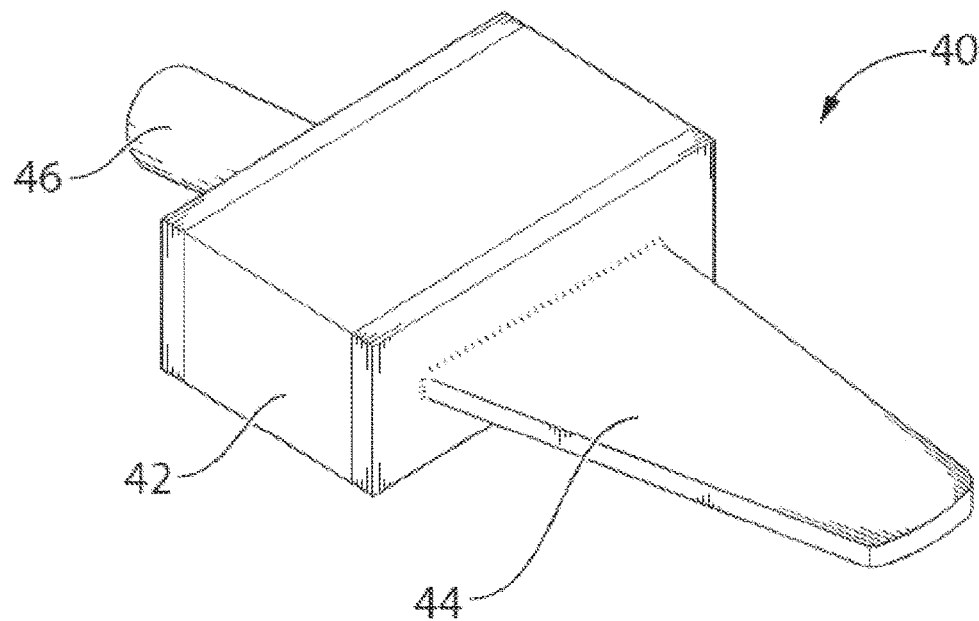
FIG. 4 is a perspective view of a magnetic device according to another embodiment, wherein the embodiment comprises a second metal portion, a magnetic portion, and a first metal portion.

Referring to FIG. 4 and according to an embodiment, there is a magnetic device 40 comprising a second metal portion 46, a magnetic portion 42, and a first metal portion 44. The terminating end of first metal portion 44 is flattened and contacts the body area of the patient that requires treatment. This embodiment, and with reference to the flattened terminating end of first metal portion 44, is amenable to narrow gaps in the body of a patient such as those in the spinal region or joints of the patient.

Figure 5:
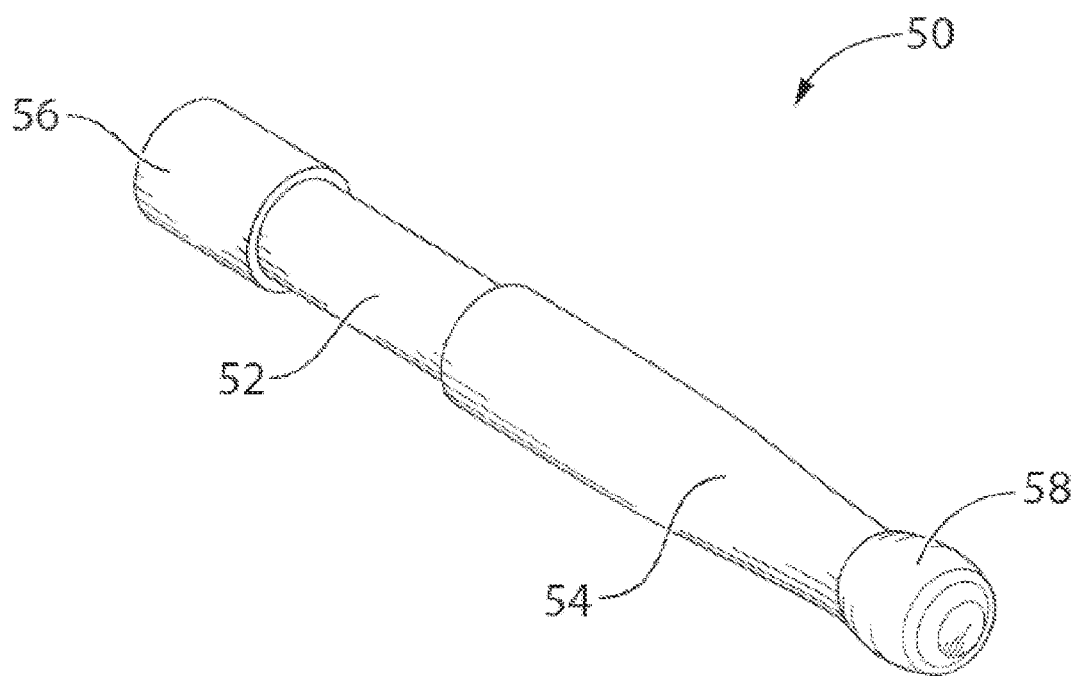
FIG. 5 is a perspective view of a magnetic device according to another embodiment, wherein the embodiment comprises a second metal portion, a magnetic portion, a first metal portion, and a head connected to the first metal portion.

Referring to FIG. 5 and according to an embodiment, there is a magnetic device 50 comprising a second metal portion 56, a magnetic portion 52, a first metal portion 54, and a head 58. Second metal portion 56 and magnetic portion 52 are shaped as cylinders. First metal portion 54 is also shaped as a cylinder but tapers as it terminates towards head 58.

Second metal portion 56 comprises a first end that faces away from magnetic portion 52 and an opposite second end that faces towards magnetic portion 52. First metal portion 54 comprises a first end that faces towards magnetic portion 52 and a second end that terminates at head 58. Magnetic portion 52 comprises a first end that faces towards second metal portion 56, and a second end that faces towards first metal portion 54. The diameters of second end of second metal portion 56 and the first end of first metal portion 54 are greater than the diameters of the first end and second end of magnetic portion 52. As such, the first end of magnetic portion 52 is partially inserted into second metal portion 56, through the second end of second metal portion 56. Similarly, the second end of magnetic portion 52 is partially inserted into first metal portion 54, through the first end of first metal portion 56. Head 58 is spherical or ovoidal, the shape of which is particularly amenable for pressure points and other small recesses of the patient's body.

Figure 6:
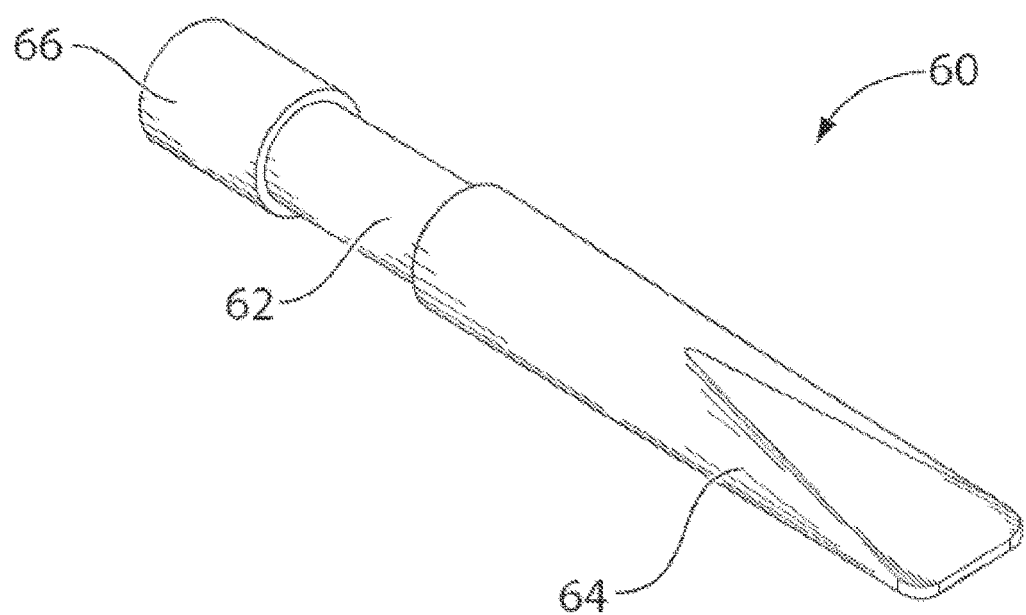
FIG. 6 is a perspective view of a magnetic device according to another embodiment, wherein the embodiment comprises a second metal portion, a magnetic portion, a first metal portion.

Referring to FIG. 6 and according to an embodiment, there is a magnetic device 60 comprising a second metal portion 66, a magnetic portion 62, and a first metal portion 64. Second metal portion 66 and magnetic portion 62 are shaped as cylinders. First metal portion 64 is also shaped as a cylinder but tapers and flattens as it extends away from magnetic portion 62.

Second metal portion 66 comprises a first end that faces away from magnetic portion 62 and an opposite second end that faces towards magnetic portion 62. First metal portion 64 comprises a first end that faces towards magnetic portion 62 and a second end that is tapered and flattened. Such a tapered end is most appropriate for addressing problems in joints or deep recesses in the body. Magnetic portion 62 comprises a first end that faces towards second metal portion 66, and a second end that faces towards first metal portion 64. The diameters of second metal portion 66 and the first end of the first metal portion 64 are greater than the diameter of magnetic portion 62. As such, the first end of magnetic portion 62 is partially inserted into second metal portion 66, through the second end of second metal portion 66. Similarly, the second end of magnetic portion 62 is partially inserted into first metal portion 64, through the first end of first metal portion 66. The tapered and flattened design of first metal portion 64 is appropriate for use in narrow gaps in the body of a patient, such as in the spinal region of the patient.

The exact shape and dimensions of the second metal portion, magnetic portion, first metal portion, and head (if included) of the magnetic device are configurable according to the body area of the patient or the severity of the disorder that is being treated. The second metal portion and the magnetic portion generally possess a round or oval shape or a shape with at least three-sides, and the following dimensional features: (i) a diameter or width/length ranging from about 0.5 inches to about 6 inches; and (ii) a thickness or height ranging from about 0.5 inches to about 6 inches, and preferably about 0.5 inches to about 3 inches. The size of the magnet will generally depend on the severity of the disorder that is treated. While generally depicted as a cylindrical shape, the second metal portion may also assume other shapes, such as a handle. The first metal portion generally has a length that ranges from about 1 inch to about 8 inches, thereby allowing the operator of the magnetic device to alter the distance between the magnetic portion of the device to the body area of the patient that is being treated. The head or the second end of the first metal portion generally has a width, length or diameter ranging from about 0.2 inches to about 4 inches.

The device may also include a non-metal cover that completely wraps around the Magnetic portion, and at least part of the first metal portion and the second metal portion. In addition, the second metal portion, magnetic portion, and first metal portion of the device may be integrally, detachably or releasable coupled together. Detachable or releasable coupling allows the operator to choose the appropriate components to treat a patient. In other words, detachable or releasable coupling of components allows the operator to customize the device.

Methods of Using Magnetic Device

In an aspect of the disclosure, there are non-invasive methods of treating disorders and/or diseases in a body of a patient. The methods of treatment involve using a magnetic device such as those disclosed herein in combination with: (i) a plurality of magnetic suction cups; and (ii) techniques such as acupuncture, chiropractic, massage, and physiotherapy. The magnetic device may comprise a permanent magnet component or an electromagnetic component, and the magnetic suction cups may be Haci™ cups.

In the first step, a plurality of magnetic suction cups is applied on the targeted treatment area(s) of a patient. N-tip and S-tip magnetic suction cups can be applied in pairs on the treatment areas of the patient, and typically in alternating fashion. This arrangement increases the strength of the magnetic field in the patient's blood in and around the treatment area(s).

Magnetic suction cups are not thought to have permanent results or lasting effects on the patient. Instead, the magnetic suction cups are used to build a magnetic field in a patient's blood, to assist the work of the magnetic device, and to calm and relax the patient's muscles and mind. The magnetic suction cups and the magnetic device can act in resonance to promote and improve well-being in the patient. Additionally, magnetic suction cups may be used to clear away a patient's waste products, and promote the natural healing of cells and tissues in the patient.

In the second step, the magnetic device is applied to the targeted treatment area(s) of the body, and pressed down for a period such as from two to five seconds against the skin of the patient in an "inch by inch" manner over the treatment areas. Particularly where treatment areas include large flat muscles, the magnetic device may be glided over the treatment areas to massage the areas with lubrication or massage oils. Generally, pressure over the contours of the body are more efficient than glide massages, and greater pressure applied for longer periods of treatment time may be required for spots that are particularly painful or deep in the treatment area(s). The length of treatment depends on the needs of the patient or the severity of the condition, and may range anywhere from 20 minutes to 12 hours. Acupoints would not usually be necessary; the magnetic device may be used to target and focus on various spots, joints, gaps, and corners of the patient that experience pain.

In problematic cases like multiple injuries or severe chronic cases, a medical professional would employ treatment strategies, such as using various combinations of treatment methods and techniques to effectively treat the deepest, most difficult, or most injured areas of the body that are unable to self-heal. Such treatment methods are akin to giving the body a "kick-start", thereby activating the body's self-healing process. Using spine disc cartilages and shoulder ligaments as examples, the misaligned spine will return to alignment and the dislocated arms will go back into the sockets automatically. In addition, the body may release toxins from the groin and glands. As a result of such treatment, all the lymphatic system and glands can regain normal functionality. Energy and mobility can be returned to the patient automatically. Once the body's immune system has been reactivated or has "kicked-in", the body can naturally heal other less problematic issues.

The treatment methods disclosed herein may be used to completely and permanently fix the causes, sources, and roots of disorders and/or diseases, and instantly cure such. Repeated or continuous treatment is not usually required. A medical professional may rely on various techniques and strategies, and rely on his own experience and knowledge to "go into", "go inside" and "force into" a patient's body to treat disorders and/or diseases, including by using hands, and thumbs, to rub and squeeze the injured tissues deeply, and to make sure that the wounded tissues receive the appropriate signals to initiate the healing process. The methods of treatment disclosed herein may be described as non-invasive surgical techniques: (i.e. no knife cuts, no use of chemicals, and no side effects). Usually, throughout the entire treatment process, no medications (natural or synthetic) need to be used. No exercise or rehabilitation is usually needed and the patient's daily routine can be his exercise. As a result of the treatment process, patients will develop a lesser dependence on, or no longer require, any previously prescribed medication.

Performance of the treatment methods may cause pain or additional pain to the patient. The worst wounds or injuries are usually treated first. The most severe pains are typically experienced at the start of the treatment process. Gradually, the pain will decrease over the course of the treatment process. Pain levels reduce when the level of severity of the wound reduces. The next day after a treatment session, the patient may experience pains or skin bruises or marks for a day or two. Some of the marks on the skin may be caused by repeated irritation of the skin or the release of toxins from, for example, spinal cord treatment. This is especially the case for spine disc treatment which require repeated and intensive pressing along the 2 to 3 inches on the disc that is treated in the direction across the spinal cord. The marks will fade over time, and is an expected part of the treatment process. The patient's spinal disc will be well instantly. In other cases, patients may experience different reactions, such as multiple bowels movements, constant urination, constant coughing for days, phlegm with blood, some fevers, or vomiting or dizziness.

The treatment methods disclosed herein do not typically cure complicated cases in patients overnight. Instead, injuries may need to be fixed or addressed one by one, or portion by portion. Pain may shift around body during the treatment process. A medical professional would be guided by the new pain to the next disorder requiring urgent treatment. In many cases, a patient may feel better for ten days, and then begin to feel pain or discomfort in a different part of the body for 3-4 days, feel better for another ten days thereafter, and then return to feeling bad for 3-4 days. The cycle repeats until the body completely recovers. The road to recovery is rough and bumpy. However, the results stemming from treatment are often better than the patient's own expectations. For example, treatment of the L-4, L-5 spine discs for back pains may also treat hip, knee and foot pains, and sexual dysfunction. Treatment of anxiety may also treat sleep, headaches, and the digestive system well, or bring about the over-night return of the ability to smell. Often, one result begets another.

The device should not be used to treat new open wounds, pregnant women, or eye balls. The treatment methods should be performed by professionals who understand body dynamics, particularly since speed, timing and the order in which treatment steps are performed can be critical in treating disorders and/or diseases. If disorders and/or diseases are not timely treated, are treated too slowly or too quickly, treated in wrong order, or not treated enough times, complications may arise such as, but not limited to, dizziness, black-outs, insomnia, or leg freeze. In extreme cases, all the hidden injuries may present themselves at once, leading to multi-severe pains.

The treatment methods disclosed herein may be used to treat common pains or disorders in areas such as the shoulder in a few sessions. However, such treatment methods mostly target long-time, chronic, severe, and multi-injuries or mysterious cases for which current medicines have no remedy. In complicated severe cases, the body cannot be treated partially or in parts. Full body cycle treatment is required and entails treating every spinal disc and detoxifying the whole body before the body can properly heal. The combination of all the methods described below (and with reference to FIGS. 7 to 13), coupled with additional treatment techniques and recovery time, can be the solution and key to reversing many otherwise untreatable disorders and/or diseases.

The different parts of the body are all related to each other and bound to each other. The buildup of toxins and injuries in a body takes many years, just like the formation of an ice mountain takes many years. With each successive treatment session, toxins are removed portion by portion. Gradually, the weight of the "mountain" is removed from the body. When the treatment reaches a critical session, the "ice mountain" will fall like an avalanche piece by piece and portion by portion until the "ice mountain" is reduced to a low amount. At that point, the immune system will "kick-in", and the body will recover and be completely and automatically cured. When the body is strong and healthy, medication has no impact on the body, like smoking, drinking alcohol or using marijuana (or other illicit drugs). Body can sleep properly, is without pain, or has no ranges of high emotions. No efforts to treat these addictions are needed. Also, exercise or rehabilitation is not so necessary. Daily life routine is exercise.

The treatment methods described herein can be used in walk-in pain clinics, and emergency room settings. Such methods may be used to treat conditions like: impending brain aneurysms or strokes, seizures, panic attacks, PTSD, chest pains, sciatic pains and dislocated or compressed spinal discs, and any pains. These methods may also be used to prevent diseases like abnormal spines which can develop and spread diseases, cause blockages in arteries before heart attacks, or cause kidney stones or failure, pancreatic dysfunction, diseases in breasts and prostates before the diseases worsen and become cancers.

The device and the treatment methods disclosed herein are low cost but have high efficacy and may be used to fix spines (and therefore serves as an alternative to chiropractic), release toxins from infections, and enhance the muscle development (and therefore serves as an alternative to physiotherapy). Like acupuncture, the device and treatment methods go deep into joint gaps, use none or some of the major meridian paths, work all over the body, and may be combined with massage therapy. The teachings disclosed herein may prevent diseases and disorders at the earlier stages, thereby avoiding the occurrence deadly attacks or cancer diseases. People will have much better health and increased longevity. Many hospitals may no longer be needed.

Provided below are embodiments of the treatment methods taught in this disclosure:

Spinal Cord Treatment

Figure 7:
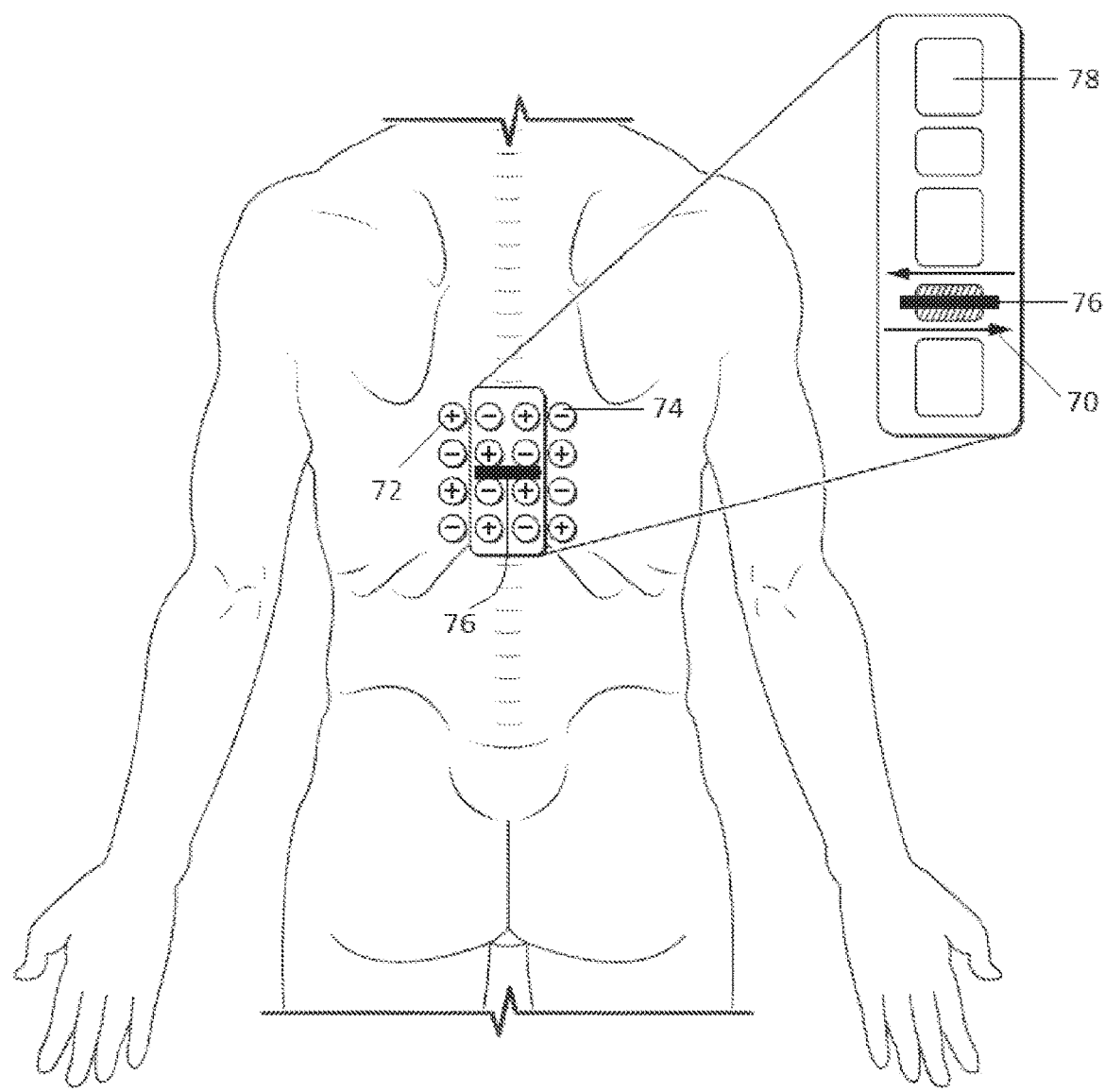
FIG. 7 is a back elevation view of a human body showing the placement of magnetic suction cups around a disordered spine of the human body, for the treatment of a spinal cord.

Referring to FIG. 7, there is a method for treating ailments in the spinal cord. A plurality of N-tip cups and S-tip cups are first applied at positions 72 (denoted by the positive circles) and 74 (denoted by the negative circles) respectively in alternating fashion. Preferably, sixteen magnetic suction cups (i.e. eight N-tip cups and eight S-tip cups) are arranged in a square around a targeted the disordered, wounded or diseased disc 76. The disordered, wounded or diseased disc 76 is preferably situated in the middle of the magnetic suction cup arrangement. The magnetic suction cups are applied along injured spine for 20 minutes or as required and are used for relaxing the muscles.

Next, the magnetic device is pressed down on top of the disordered, wounded or diseased spine disc 76 situated between two vertebrae 78. A two to three inch parallel horizontal line traversing the spine column and over the disc 76 is repeatedly press down and moved back and forth across the spinal column and over the disc 76 (as depicted by the arrow pairs 70) for 20 to 30 minutes or as required by the condition. Joints will loosen up, and the disordered disc 76 will be cured instantly. Only severely damaged discs require second treatment.

Pressing the magnetic device over the disordered disc 76 will cause pain. Applied pressure may be gradually increased according the patient's pain tolerance until the pain is reduced or until the pain no longer increases. All of the diseases or disorders in the spine disc may be treated including, but not limited to, degenerated, bulging, herniated disc, thinning disc, osteophyte formations, any abnormal discs, and conditions including meningitis of the spinal cord. The magnetic device in this method is used to break down germs, viruses, toxins, inflammations, and bacteria from cartilage. Many spinal injuries do not affect only a single disc, and often affect a number of spinal discs or a bundle of consecutively injured discs. By fixing each successive disc, spine recovery will be enhanced.

The magnetic field strength of the magnetic device not only treats the outside of the spine, but also may influence the inside of the spine cord where there may be lesions, clots or viruses that cannot otherwise be removed. Such lesions, clots or viruses also block the vital channels for blood and energy flow. By performing successive spinal disc treatments one after another, a stronger magnetic field strength is built up, which may result in the breakdown of existing clots, lesions and viruses inside the spine cord. All unwanted waste products are excreted. When the vital channels are open, the body's energy returns, and the body is straight. Each spine controls a portion of the body's muscles or organs directly or indirectly from the neck to the feet. Abnormal spines can cause damage to the entire body by deteriorating organs and allowing diseases to develop. The spine is like a train station. If a train station is not functioning properly, the railway cannot deliver food, nutrition, or oxygen to the body. When the spine is dysfunctional, the spine will send the wrong signals to nerves, leading to attacks on good tissues. This is otherwise known as an "auto-immune disorder. No current medicines can cure an illness without remedying the associated auto-immune disorder. To remedy the disorder, spinal discs have to be fixed. Abnormal spines may also lead to brain disorders such as brain tumors and the development of tumors along the spine, and cause mental illness like extreme emotions or hallucinations. Such mental illnesses may be treated by a combination of spinal cord treatment and brain and central nervous system treatment, which is described below. The spine is the cause and source of the most diseases and disorders, except for intruder diseases or otherwise.

Example 1

Patient is not able to swallow or eat properly. Food is constantly stuck in his throat or fails to enter the esophagus. C-1 to C7 spinal discs are treated. Patient regains function of throat. Such treatment is also amenable to treating amyotrophic lateral sclerosis, which is a major issue.

Example 2

Patient constantly feels sharp pain in chest, cannot breathe deeply, cough or sneeze. Patient's T-6 spinal disc is fixed, and all symptoms disappear instantly and forever. Disorders with the T-6 spinal disc are also major causes for lung disease. Fixing T-3 to T-6 spinal discs prevent formation of blockages in the arteries before heart attacks, and diseases leading to breast cancer.

Example 3

80-95% human populations suffer from L-4 and L-5 spine disc diseases or disorders. These two discs are also related to the hip, knees, feet, prostate, bladders, infertility, and kidneys. If these two spinal discs are fixed, a large population can get their lives back.

Example 4

Patient, 71 years old, is diagnosed with multi-degenerative spine. Patient wears pace maker for heart, and has history of passing-out. Her uterus and one of her ovaries are removed. Patient has severe pains on low abdomen when she walks into the clinic. She has burning, itching skin all over her hip, legs, feet, and required urgent treatment. After receiving spinal cord treatment for each disc, the pain that she had experienced for the previous 40 years disappears forever and she never has heart attack after.

Example 5

Patient in his 60s has history of severe back pains, and many times ended up in emergency. Patient also has stones in his kidneys. After receiving a few treatment sessions for his pain, patient suddenly experiences severe pain at night. Emergency X-ray reveals that his biggest kidney stone has come out and is stuck in the ureter. After a couple more treatments, the stone is expelled during urination. The remaining smaller stones do not cause any pains and are passed without his knowing. Pain is gone forever. In this case, the stone unexpectedly passes during back pain treatment.

Example 6

Scoliosis can be instantly fixed, the spine can shift back into alignment if the case is not severe. If severe scoliosis, the treatment process will be as same as that for chronic fatigue syndrome.

Brain and Central Nervous System

Figure 8A:
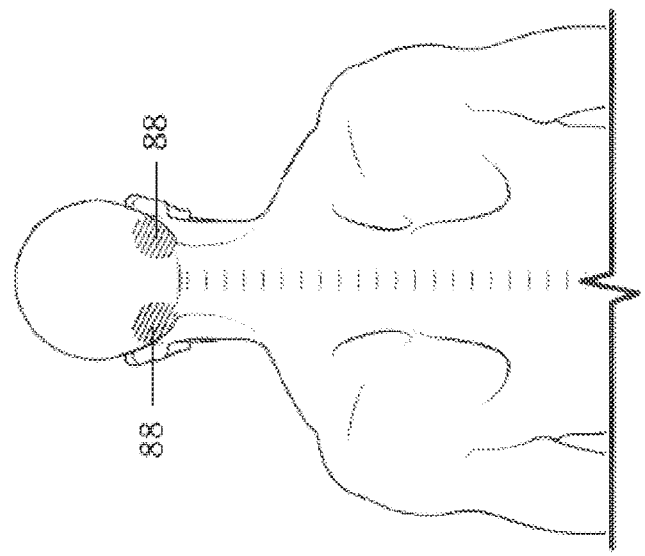
FIG. 8A is a back elevation view of a human body showing the placement of magnetic suction cups on the neck and shoulder regions of the human body, for the treatment of disorders in the brain and central nervous system.
Figure 8B:
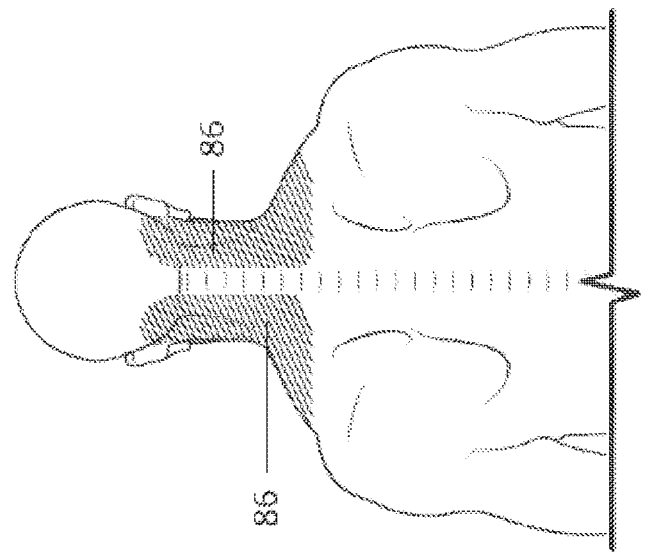
FIG. 8B is a back elevation view of a human body showing the neck and shoulder regions of the human body, for the treatment of disorders in the brain and central nervous system.
Figure 8C:
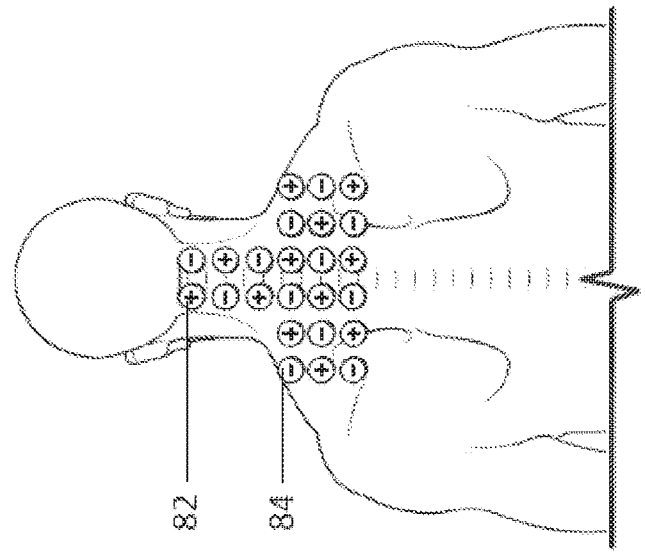
FIG. 8C is a back elevation view of a human body showing the occipital region of the human body, for the treatment of disorders in the brain and central nervous system.
Figure 10A:
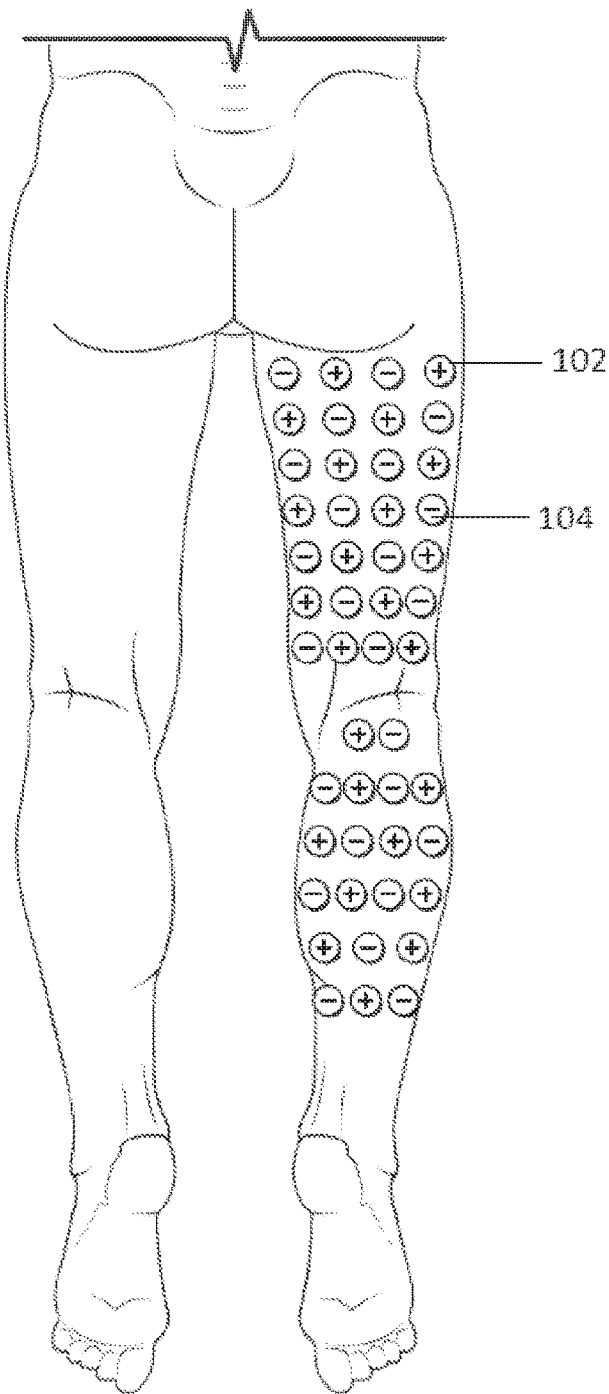
FIG. 10A is a back elevation view of legs of a human body showing the placement of magnetic suction cups on the hamstring and calf regions of a right leg of the human body, for the treatment of disorders in the right leg.
Figure 10B:
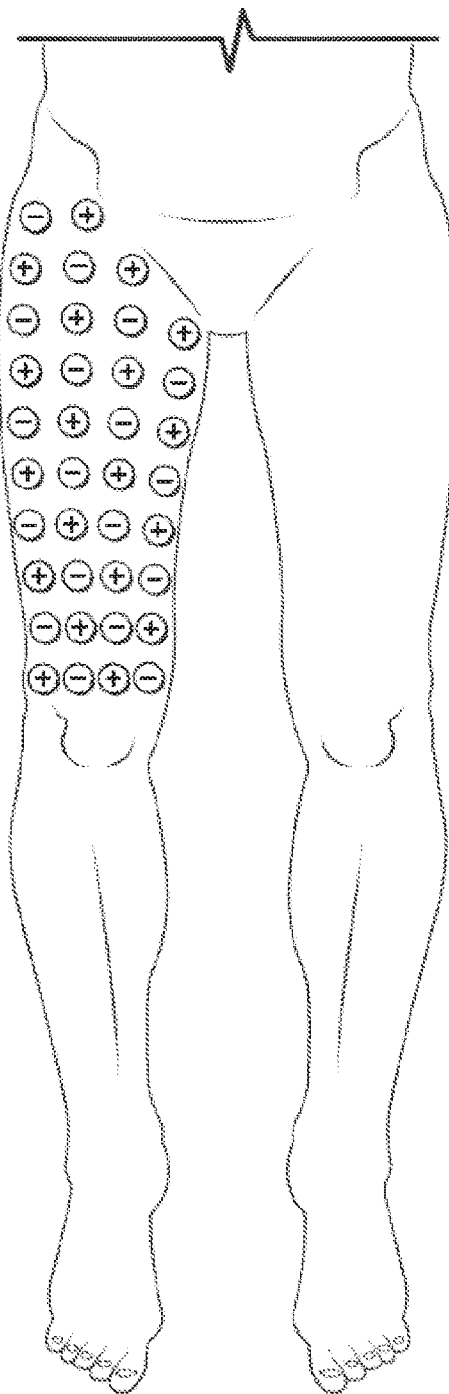
FIG. 10B is a front elevation view of legs of a human body showing the placement of magnetic suction cups on the quadriceps region of a right leg of the human body, for the treatment of disorders in the right leg.
Figure 11B:
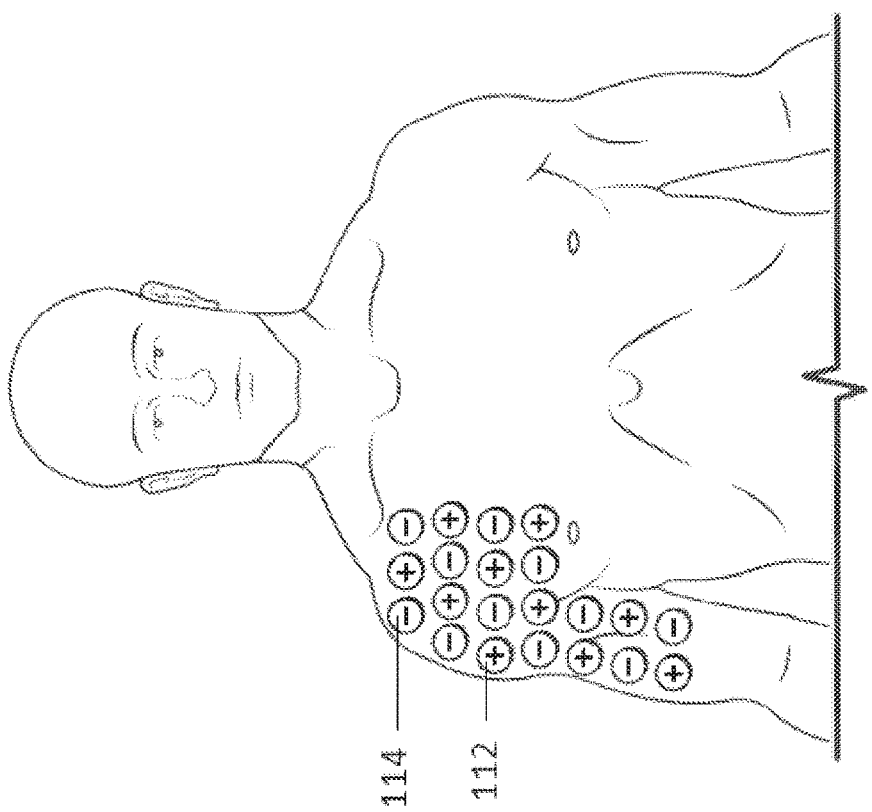
FIG. 11B is a front elevation view of a human body showing the placement of magnetic suction cups on the right pectoral region of the human body, for the treatment of disorders in the right arm.
Figure 11A:
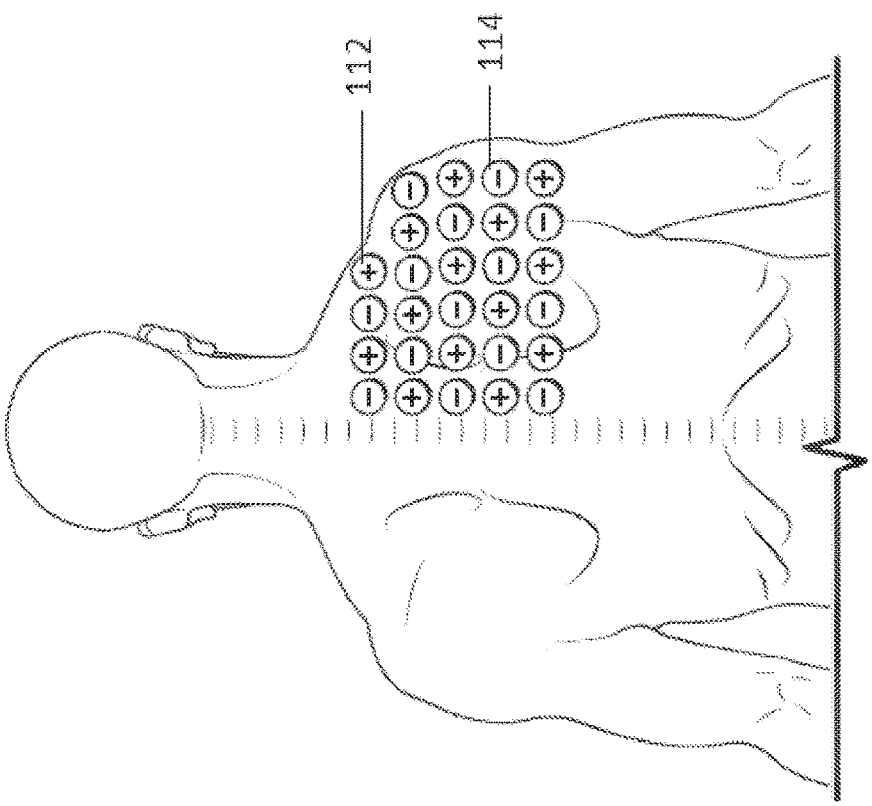
FIG. 11A is a back elevation view of a human body showing the placement of magnetic suction cups on the right scapula of the human body, for the treatment of disorders in the right arm.

Referring to FIGS. 8A to 8C and according to an embodiment, there is a method for treating disorders in the brain and central nervous system. A plurality of N-tip cups and S-tip cups are applied in alternating arrangement at positions 82 (denoted by the positive circles) and 84 (denoted by the negative circles) respectively, in the neck and up-shoulder and back treatment area 86 for 20 minutes or as required. 20 to 30 magnetic suctions cups are typically used to build the magnetic field in the blood flowing into the brain, to speed up blood circulation to wash away unwanted waste products like toxins and chemicals.

Next, the magnetic device is applied on the neck, and pressed down from the back of the head to the top of the shoulders. Referring to FIG. 8B, and specifically the neck, upper-shoulder and back treatment area 86, this action is repeated back and forth for 10 minutes on each side of the neck. The pressure applied varies depending on the person. In many cases, the greater the pressure, the better. Treated areas included the occipital belly, suboccipitals, trapezius, splenius capitis and splenius cervicis, greater auriculare accessory nerve, levator scapulae, internal and external carotid arteries, and Vagus nerve. This treatment method breaks down clots and loosens muscles and specifically unlocks the neck muscles. Referring to FIG. 8C, sharper or stronger embodiments of the magnetic device may be applied on the occipital regions 88 for 5 minutes on each side. Press deeply, repeatedly and intensively on these regions 88. Some addition pain spots may require for more treatment time.

Occipital regions 88 include, hut is not limited to, the occipital artery greater occipital nerve, lesser occipital nerve, third occipital nerve. The occipital regions 88 are the gate through which blood vessels and nerves access the brain. Keeping the gate open is important for bringing in blood and allowing nerves to maintain their function. Using the magnetic device repeatedly and intensively and working around the gate breaks down blood clots or blockages, releasing unwanted chemical germs, and stimulates tendons, ligaments, and nerves in the occipital regions 88 that are the nearest to the inside of the brain. Blood circulation washes away unwanted waste products, chemicals, inflammations, assists in the natural repairing of ruptured vessels, and rejuvenates and heals nerves and scar tissues. Brain and central nervous system treatment can treat all the brain diseases and disorders, and is the premier treatment for any severe chronic cases. Younger people seem to respond more favourably to this treatment than older people. Brain and central nervous system treatment can treat anxiety, migraine, insomnia, impending brain aneurysms, eye disorders, eating disorders, dementia, severe depression, ADHD, concussions, meningitis, epilepsy, speech disorder, dizziness, panic attacks, PTSD, all brain and center nervous system diseases and disorders. Said treatment is amenable to waking up those in vegetative states (but whose brains are still functioning), or those who are in early stage coma. Said treatment also has a cosmetic impact, and may allow people to look ten years younger in some cases. However, the effect only lasts for about a week.

Example 1

(a) Patient is treated for depression, the result come with the period she hasn't had for years. (b) Patient is treated for untreatable acne whose face has turned black for many years. Treatment results with gas flow in low abdomen. Locked neck is unblocked and patient regains mobility.

Example 2

Patient suffers from migraine for all her life. Migraine affects her an average of 20 days per month for 22 years. After one treatment, patient experiences one more severe headache the next day, after which her migraines never return.

Example 3

Patient in 30s has history of anxiety, severe headaches, and depression and is treated for such. The next day after treatment, she experiences unexpected results. She has two portions of skin "rashes" on her orbicularis occuli muscles and 2 soy bean bumps on top these rashes. Gradually, her skin "rashes" fade, though the soy bean bwnps take more time to go away. No treatment is ever performed close or near the eyes. All treatment is performed on the back of her head. It is believed that the toxins and inflammation are cut off, and a portion of the toxin goes into the eye's orbicularis occuli muscle, and is ultimately removed from between the back of the neck and eye balls. The treatment may be used to treat to all the eye diseases or disorders such as blurred vision, double visions, itchy eye balls, tension, dry and watery eyes.

Example 4

Patient in later 30s, cannot eat properly for 7 years, and cannot sleep properly for 5 years. Patient depends on a clock to eat meals, because he never feels hungry. Patient receives brain and central nervous system treatment, combined with detoxification for six sessions, after which he is able to eat and sleep well.

Example 5

Patient in his 30s is a professional athlete who requires urgent treatment for severe headaches combined with "hits" which feel as if he is being hit with a baseball bat. He has a history of severe headaches for 3 years, and uses any medication. He maxes out on his doses. No modern methods are of assistance to him. He also sees many experts for help, but to no avail. After this treatment, the headache "hits" disappear right away. He is able to sleep at night, and the following day he receives a second session of the same treatment. His headaches are reduced to 20%-30% of previous pain. Patient no longer experiences any more 'hits'. It is believed that the treatment saves the patient from an impending brain aneurysm, which never comes back.

Example 6

Patient 23 years old. Walks into clinic with pale face (white face) and suicide on his mind. He is on anti-depression medication for ADHD some time. The medication is making him feel worse and worse. He tries to stop take these pills, but almost passes out because of withdrawal symptoms. Patient receives brain and central nervous system treatment. He goes home and begins to have big bowel movements for many times. Prior to this occurrence, he hasn't had bowel movements for a long time due to the medication's side-effect: that is, constipation. A few sessions after, his face looks fresh, he no longer has suicidal thoughts, and no eye drops are required. His condition is reversed back to where he is before he started taking medications. He has a foggy mind. After receiving a number of treatments for his physical injuries, he returns to normal. Patient no longer takes medication, even though no efforts are made to achieve such. He is cured completely.

Sciatic Nerve Treatment

Referring to FIGS. 9A and 9B, there is a method for treating the sciatic nerve pain. A plurality N-tip cups and S-tip cups are applied at positions 92 (denoted by the positive circles) and 94 (denoted by the negative circles) respectively in alternating fashion and across the lower back and upper buttocks area. Thirty-two cups are depicted in FIG. 9A. However, the number of magnetic suction cups that is used may vary. The magnetic suction cups are first applied to the treatment area for approximately 20 minutes or as required. It is believed that the magnetic suction cups assist blood circulation into the buttocks.

Next, deep tissue massages is performed by using hands, thumbs or non-magnetic deep tissue massage tools all over the butt region 98. To perform deep tissue massage, one must press down hard, and squeeze and twist all over the lower back and buttocks including the thigh, hip, and gluteus maximus. Hand deep tissue massages promote blood flow more efficiently, and also release any blood that may be trapped inside the bottom of the buttocks. Currently used magnetic devices are not as efficient as hand deep massages.

Next, the L-4 and L-5 spinal discs (91, 93) are treated, resulting in permanent cures.

The sciatic treatment can treat the worst sciatic pain instantly. No medication or current methods can compare. There are two pools of blood trapped inside the bottom of the buttocks region 98. Buttocks is blocked from other part of body. Blood is unable to flow in and out. Tissues and nerve cells begin deteriorating inside. Deep tissue massages unblock vital channels so that the fresh blood can go in, and trapped blood can be released from the buttocks. Should waste blood not be removed, such waste can deteriorate or eat away the hip joints from the inside of the buttocks, and strike sciatic nerves. Removal of these pools of blood is therefore very important for body healing processes from the bottom of the buttocks region 98. In addition to deep tissue massages, L-4 and L-5 spinal discs may be fixed to ensure a permanent cure. Sciatic treatment is one of the top three premier treatments, along with brain and central nervous system treatment, and spinal cord treatment. Sciatic treatment is required to be used in every severe cases. It is important to first act on or start with chronic serious conditions.

Example 1

Patient in her 60s suffers from a history of spinal problems, and has surgery on the L5 vertebrae two years prior to sciatic nerve treatment. Pain medication is unable to alleviate her sciatic nerve pains. Many methods are useless. As a result of the pain, patient does not want to live anymore, and requests urgent sciatic treatment. After an hour period of sciatic treatment, the pain is completely gone. The following day, dark bruises appear on either side of patient's buttocks. Patient undergoes follow-up detoxification treatment on her thighs, hips, IT-bands, hamstring, quadriceps, calves, back of the knees and groin. Years of toxins surface to the skin, forming what looks like dark bruises. During treatment sessions, she experiences vomiting, felt sick and has many big bowel movements. Patient's L-4 and L-5 discs are treated, and she was cured completely.

Leg Treatment

Referring to FIGS. 10A to 10E, there is a method for treating disorders in the legs. Using the right leg as an example, a plurality of N-tip cups and S-tip cups are applied at positions 102 (denoted by the positive circles) and 104 (denoted by the negative circles) respectively in alternating fashion and over an affected leg area. The magnetic suction cups relax the muscles and calm the patient down.

Next, the magnetic device is used to press the whole leg, and particularly over areas back 107, side 108, and front 109 of the leg. Detoxification of IT-bands, hamstrings, quadriceps, calves, back of knees 103 and groin 101 is performed. Toes 100, ankles 105a, ligaments 105 between the shinbone and surrounding muscles, and ankle joints 109a are optionally treated.

Next, the L-4 and L5 and other disordered spinal discs are treated.

Leg treatment is used for all the issues involving the legs, such as muscle pains, cramps and stiffness; the joints for knees, ankles, groins or ligaments, tendons, muscles tears, sprains, abnormal hernia, drop foot, and plantar fasciitis. In some not severe cases, the pains at the bottom of the foot can be instantly stopped by treating L-4 and L-5.

Example 1

Patient in 30s suffers from severe pain at the bottom of heel and around ankle. Pains shoot from her hip to the bottom of the leg for years. She tries medications and injects cortisone shots in the ankle. She also undergoes years of physiotherapy. In this case, she needs to combine leg treatment and healing damaged muscles with use of the magnetic device, which is applied on the wounded tissues of foot repeatedly. The wound tissues on foot cannot be fixed instantly. Otherwise it would be too painful to force healing. Such healing must be gradual and takes time. Pressure is increased gradually. The condition that she suffers from is "plantar fasciitis", and through the treatment her pain is gone forever. Leg treatment included detoxification and healing the whole leg. Spine disc L-4, L-5, S-1 are also treated.

Example 2

Patient in later 30s suffered from severe pain in groin. The pain is too much for a big guy. During his MRI exams, he bites his tongue to reduce the intensity of pain in the groin. It is hopeless to find any help. In this case, the magnetic device is used to work on the groin. Repeated and intensive detoxification. Healing of the groin joints occurs while performing treatment on L-4, L-5 spinal discs and sciatic treatment. His pain disappears and his life returns. In this case the patient has overwhelming inflammation and toxins accumulation from injuries. L-4, L-5 may produce too much toxin for lymph to remove. The toxins released from the groin helps lymph function and repair the ligament tendon tissues. Groin is the major areas of lymph nodes and toxin accumulation can turn into abnormal hernia if not cleaned up.

Arm Treatment

Referring to FIGS. 11A to 11D, there is a method for treating disorders in the arms. A plurality of N-tip cups and S-tip cups is applied at positions 112 (denoted by the positive circles) and 114 (denoted by the negative circles) respectively in alternating fashion and over the scapula and pectoral regions of the patient. The magnetic suction cups are applied to the treatment area for approximately 20 minutes or as required.

Next, treating the scapula 111 is the priority for all issue involving the arms. Some pain spots need to be repeatedly pressed on. Specifically, the magnetic device is pressed all over the arm from the acromioclavicular joint 113, upper-arm (cuff) 115 to elbow 117 and wrist 119. Importantly, one should be guided along the tendons, joints or gaps of muscles to where the pain locations are. Repeated focus at pain spots such as tennis, golf spots, or AC joints, wrist joints, target pain locations may be required. Shoulder joints are connected for ligament and tendons, lymphs. Special attention is required detoxification and healing.

Next, check if patient has spine injuries along T-1 to T-6 spinal discs. If an injury is present, auto-immune system will attack the shoulders. This treatment may be used to all the issues involving the shoulders, arms, elbows, and hands, including "tendonitis" in the shoulders, tennis or golf elbow, carpal tunnel syndrome, arthritis in the fingers, pins and needles in fingers, and dry or sweaty hands.

Example 1

Patient has history of no arm strength, to the point that he is unable to hold a glass in his hand. His hands experience "numbness" at night, and he cannot feel hot or cold water. After a few treatments of the disclosed treatment methods, patient is able to work, and his "numbness" disappears. He also receives treatment of spine discs T-1, T-2, and T-6.

Example 2

Patient in 30s suffers from a rare disorder. She has psychological stress and two palms of dry skin. Drugs and methods do not help her. She receives treatment for her emotions, and scapula treatments on each side. After treatment, she is cured forever. This same treatment may be used to reverse the condition of sweaty hands.

Treatment of Sinus, Hay Fever, TMJ, and Tinnitus

Referring to FIGS. 12A to 12D and according to an embodiment, there is a method for treating sinus, hay fever, temporomandibular joint disorder ("TMJ"), and tinnitus. The brain and central nervous system treatment is first performed. Second, neck spine injuries (if any) are detected and fixed.

Figure 12A:
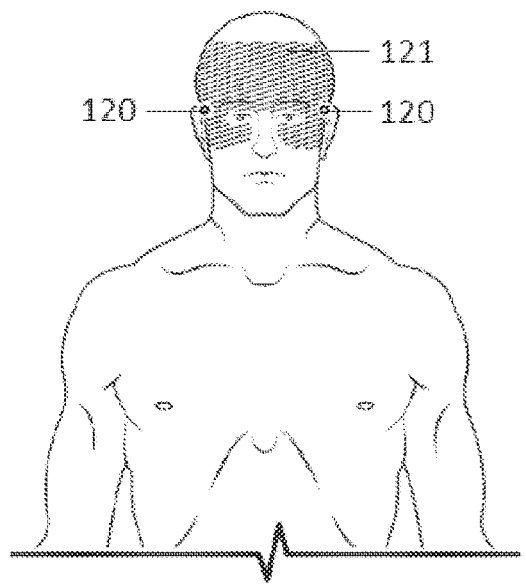
FIG. 12A is a front elevation view of a human body showing the head region of the human body, for the treatment of the sinuses.

Referring to FIG. 12A and with regard to the treatment of sinuses, pressure is over the forehead in head region 121, under the eyes, on the temples 120, and on the occipitofrontalis muscles, and zygornancus molar muscles.

Figure 12B:
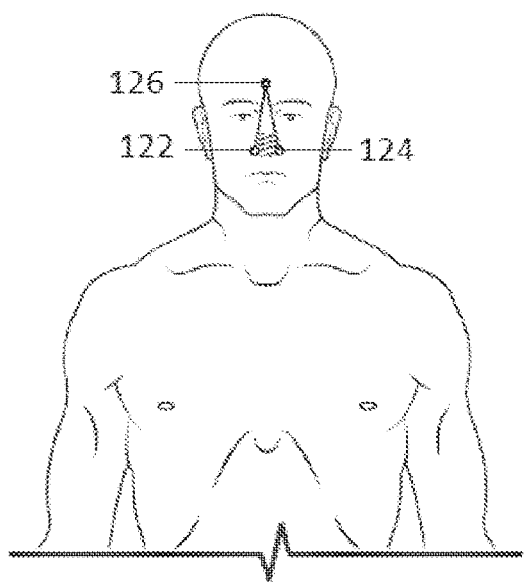
FIG. 12B is a front elevation view of a human body showing the nose and the glabella of the head region of the human body, for the treatment of hay fever.

Referring to FIG. 12B and with regard to the treatment of hay fever, pressure is applied on each side (122, 124) of the nose, and on top of the nose, including the glabella 126, limen nasi, and nasal vestibule.

Figure 12C:
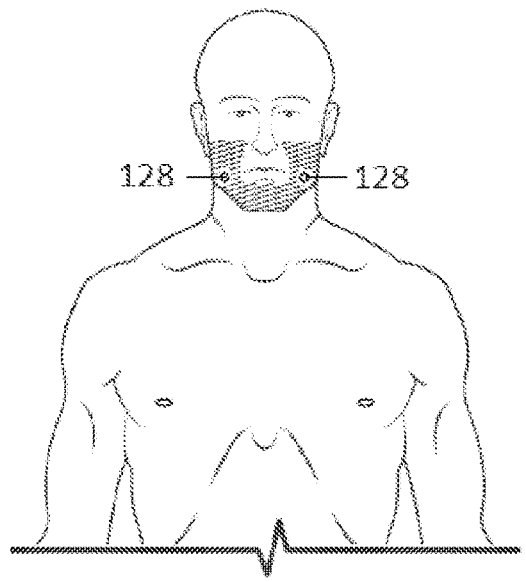
FIG. 12C is a front elevation view of a human body showing the head region of the human body, for the treatment of temporomandibular joint disorders.

Referring to FIG. 12C and with regard to the treatment of TMJ, pressure is applied to the jaw muscles in general, and particularly the gland massater, the buccinator muscles 128, the paroid gland and the facial n., and maxillary a.

Figure 12D:
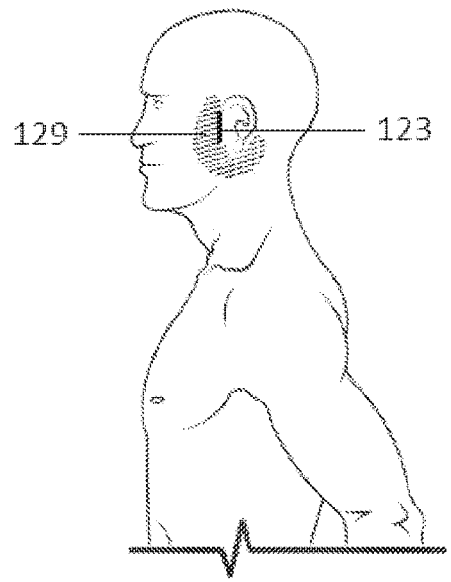
FIG. 12D is a side elevation view of a human body showing the left side of the head region of the human body, for the treatment of tinnitus.

Referring to FIG. 12D and with regard to the treatment of tinnitus, pressure is applied around the ear area 129 and particularly at the area where the ear meets the face as depicted by item 123, the auricular n., maxillary a., posterior auricular a. and posterior auricular n. within ear area 129, all of which are in the gaps around the ear.

Example 1

Patient 40s suffers from seasonal sinus disorder, running nose and tears. Patient receives Brain and Central Nervous System Treatment. Pressure is applied through the magnetic device over his forehead and around his eyes and temples 120. Sinus stops instantly and for a long time, if not forever.

Example 2

Patient in 60s both with long time TMJ, dental adjustment, or mouth guard. Patient cannot stop grinding and clenching his teeth at night. For treatment, pressure is applied all over the jaw muscles and glands. Work is repeated on the pain spots. After add-in, cervical vertebrae injury treatment is performed, and TMJ is cured.

Neck and Trunk Treatment

Referring to FIGS. 13A and 13B, there is a method for treating the neck and trunk. A plurality of N-tip cups and S-tip cups are applied at positions 132 (denoted by the positive circles) and 134 (denoted by the negative circles) respectively in alternating fashion and over one or more of the pectoral and shoulder region 136, neck and spinal region 138, and groin region 139 of the patient. Magnetic suction cups are only applied to the areas which need to be worked on (see FIGS. 13A and 13B).

Next and referring to FIGS. 13C and 13D, the magnetic device is swiped inch by inch along the neck, with focus at the sternocleidomastoid and where lymph nodes and lymphatic vessels are. With regard to the back trunk, the magnetic device is swiped inch by inch from top of shoulder to the low extremities (tail bones) along both sides of the spine. The back trunk includes, but is not limited to, the trapezius, iliocostalis, and lumborum. Pain spots are worked on repeatedly and for a duration as required. This large area of muscles can be separately worked on depending on patient s wishes or time. Front trunk chest area 136 and low abdomen area 139 include the pectoralis majors and the area from the level to L-4, L-5 to lowest extremities abdomen, respectively. In present treatment method, sternums and ribs are not major issues unless there are pain spots. Abdomen is automatically treated with the spine treatments, unless otherwise noted.

These treatments are for large muscle areas where toxins accumulate. If large portions of toxins can be removed from these large muscle areas, and all the muscle issues like stiffness, cramps, and pains can be avoided. Specifically, pneumonia, eating disorder, insomnia and dementia may be treated by the combination of neck and trunk treatment and brain and spinal cord treatment.

Example 1

Patient in 30s, has accident 18 years ago. Spinal discs L-4 and L-5 are severely dislocated. No other methods can reverse the spine. Treatments on each disc after, patient finds her back loosening. Within a few day to two weeks she experiences a big "click". The dislocated spine shifts back into alignment. Patient also has complications like severe sciatic, anxiety, and annual pneumonia. A couple of degenerated spinal discs L-3, T-6 are treated, and detoxification of the full trunk is done to remove toxin build up that has accumulated over these years. After the treatment, all the complications are fixed, and pneumonia never comes back.

Example 2

Patient has rare diseases. Lesion grow all over his penis and testicles. For 15 years, he is unable to have sex, and has complications with pains in low back and knees. During the treatment, patient can see lesions disappearing before his eyes. His L-4, L-5 spinal discs and sciatic are also treated. He is able to have sex again and without pain.

Treatment of Severe Multi-Injuries and Chronic Mysterious Illness

The body cannot be treated partially or just at pain locations. Body is all related. In the case of severe multi-injuries and chronic mysterious illness, every single spinal disc from C-1 to the tailbone and full body details need to be treated, and detoxification and healing steps are required. It's a bundle illness for developed and reversing it. The treatments are the same to all severe cases. Combine all the above example treatment methods from FIG. 7 to FIG. 13 of how to treat various parts of the body. The priority treatment methods, however, are: (i) brain and central nervous system treatment; (ii) sciatic treatment; and (iii) treatment of disordered discs. The rest of treatment all follow the pains and work all over the body follow priority pains. Full body detoxification and healing are repeated more than once, as required. In some cases, treatment may require longer periods of time and detail, and extra work.

All the diseases and disorders can be treated including, but not limited to, Parkinson's disease, MS ("multiple sclerosis"), paralysis, lupus, ALS Lou Gehrig's disease), scoliosis, fibromyalgia, diabetes, meningitis, bi-polar disorder, CTE (chronic, traumatic encephalopathy), and CFS (chronic fatigue syndrome).

Case 1: Patient in 30s is involved in two motor-vehicle accidents and suffers multiple injuries to the spine. He experiences severe pain all over his body, and also suffers from anxiety and insomnia. Within the preceding four year period, he tries all methods or medicines to better his condition. After two years of medication, however, his stomach starts to feel sick because of ulcers resulting from taking too many pain-killers. He is unable to cope with life. He receives treatment disclosed herein for two months. After that, he is able to live without pain strikes. Three to six months later, he recovers and returns back to normal, and walks out a free man.

Case 2: Patient in 30s is diagnosed type 1 diabetes from age 9. Doctors announces that her pancreas would never be able to produce insulin. She wears an insulin pump every day and night for these years. Years later, she develops more issues like ADHD and the thyroid, and thus takes ADHD and thyroid medication. After brain and central nervous system treatment, the next day patient starts to have enormous bowel movements, due to constipation. After treatment of the T-8 to T-12 spinal discs, her insulin meter dosages begin to drop rapidly, thereby indicating that her body consumes less external insulin and that her pancreas begins to produce insulin again. T-3 to S-1 spinal disc treatment is performed, after which her legs (Charley horse) stop shaking at nights. Her body recovers rapidly. Insulin doses drops significantly. She regains more energy to work and play. Her body straightens. During the period of treatment, her response to the treatment is volatile. One day is good, but the next day is bad. One problem is fixed, but another starts somewhere else. Exemplary problems include skin hives, feeling sick, or pains. During her treatment, she progresses 10 steps, falls back 3-4 steps, and then progresses a further 10 steps, and then regresses 3 to 4 steps back. Such a cycle continues until she becomes completely well. No efforts are made to treat her thyroid. However her thyroid automatically recovers because less toxins are produced by her body, and detoxification helps clean the thyroid gland. Medications for ADHD and thyroid are off completely.

Case 3: Patient in 30s is diagnosed MS for one year. She experiences double visions, headaches, stiffness in her muscles, some pains from groin and calf "central interosstous membrane". MRI shows she had lesions in her brain and spine. All of these symptoms are removed very easily except the lesions in her brain. In addition, the treatment of MS requires some strategies, including:
 a) brain and central nervous system treatment can instantly treat eye disorders and headaches. Such treatment can also start the process of repair the scar tissues and removing clots from brain, thereby allowing chemicals and germs to be washed away, and starting the body's natural healing and rejuvenation process. Repeating said treatment may result in reducing and weakening clots and lesions;
 b) disordered neck spine discs are fixed. Such fixing can break down the lesions in the spine and stop such lesions from extending into the brain; and
 c) detoxifying and healing tissues around neck and upper body, such as scapula and inter scapula, chest muscles, upper arm, including the trapezius, deltoid (best including all trunk back muscles), AC joints, and shoulder joints. Detoxification and healing of such areas cuts off supplies to the lesion, while weakening any lesions inside the brain, disconnecting any chains of lesions, and stopping lesion supplies into the brain. The lesions inside eventually will break down.

After 20 treatments, patient experiences severe headaches, and feels sick. The next day instead of being worse, she finds herself to be full of energy, free of headaches, and stronger after many years. She is further examined by MRI, where it is discovered that the lesions in her brain and spine has disappeared, in this MS case, full body intensive treatment follow-up is required until she is completely treated. Without such follow-up, lesions will grow back.

Case 4: Patient in later 50s, has chronic fatigue syndrome (CFS), and his body is always very tight and stiff. He is also always tired and sleepless. The older he gets, the worse he becomes. He can fall asleep anywhere, regardless of time, location or occasion. However, he has trouble sleeping or entering deep sleep at night. Every spinal disc from C-1 to the coccyx was treated. Patient underwent complete detoxification and healing cycle. His body loosens and relaxed over time. He uses a sleep monitor every night, he finds that he is able to sleep deeply after the treatment. As a side note, brain and central nervous system treatment can help a patient achieve sleep, but body injuries or other issues in the body may also cause sleeplessness. As such, the entire body may need to be cured. In this case, maintenance is required after treatment. For example, Haci™ cups are first applied along the entire length of both sides of the spine from the C-1 spinal vertebra to the tailbone to loosen the spine and muscles surrounding the spine.

Then, massage or massage tools known in the art is performed or used to strengthen the patient's core and keep the spine loose and in alignment. Such treatment may also be amenable to treating severe scoliosis.

Case 5: Patient in 30s has been paralyzed for 12 years after two strokes. The first stroke is a mini stroke. However, his second stroke is a big stroke, and he is paralyzed after that. He received acupuncture intensively, is able to transition from a walker to a cane. After that, he has no more progress from acupuncture. He stops receiving acupuncture therapy and instead uses physical exercises to rehabilitate his body. He begins to swim daily and uses handwriting to exercise his arms and hands muscles. He also does push ups daily. He walks in the inventor's clinic with a cane on which he leans heavily. He drags his legs, his speech slurs, and doctors implant a bloom in his blood vessels to prevent blood clots from flowing into his brain. According to him, he still has blood clots in the vessels and he is taking blood thinner medication daily. A month after treatments, patient finds that he is able to swim pain-free, go out without a cane, and walk up and down stairs with little help from the railings. His speech also greatly improves. Three to six months after, he walks like normal person without cane, his speech is clear, and his writing is much more legible.

Case 6: Patient is diagnosed with Parkinson's disease for 26 years. She is on prescriptions drugs and took 13 to 15 pills per day. Every three hours she has to take pills, or her tremors would strike. She carries food with her wherever she goes and takes food all the time. The foods do not stay in her body for long, and she has to go to the toilet 20 minutes after eating. She suffers from anxiety and depression and searches for experts all over the world. In this case, the treatment is no different from any other severe case. Each spinal disc is treated, and she undergoes full body detoxification and healing. However, her reactions are volatile and extreme. One week after treatment, she is able to walk a few blocks away without help, and can take food without having to go to the washroom until the next day. Every day she has a bowel movement, sometime big, sometime smaller. However, every 10 to 15 days, she has violent bowel movements, more than 10 times a day. For those days, she cannot leave the toilet too far or finning out time. This cycle repeats for many times. Each time and after these big violent bowel movements, she returns with a better level of condition. She improves one level by one level, and gets stronger and stronger. Finally, the toxins which have accumulated in her body for many years, come out and are removed. Six months after, she is in great condition, she no longer experiences tremors, and her body is stabled. This is miraculous. Medications no longer have an influence on her body, and are automatically excreted. When the body is strong and healthy, patient will find that addictions such as smoking, alcoholism, or drug dependence, will be easy to get rid of.

Other Embodiments

It is to be understood that while the invention has been described in conjunction with the detailed description thereof and accompanying figures, the foregoing description and accompanying figures are only intended to illustrate, and not limit the scope of the invention, which is defined by the scope of the claims in the disclosure. Other aspects, advantages, and modifications are within the scope of the following claims.

I claim:

1. A device for massage or inch by inch press treatment of a physical disorder or disease in a patient, the device comprising:
   a magnetic portion, wherein the magnetic portion has a first side and an opposite second side;
   a first metal portion, wherein the first metal portion has a first end and a second end; and
   a second metal portion configured for hand holding, wherein the second metal portion has a first side and a second side;
   wherein the second side of the second metal portion: (i) is coupled to the first side of the magnetic portion; and (ii) has a surface area that is less than the surface area of the first side of the magnetic portion; and
   wherein the first end of the first metal portion is coupled to the second side of the magnetic portion and the entire first metal portion extends away from the magnetic portion in a direction opposite to the second metal portion.

2. The device as claimed in claim 1, wherein the magnetic portion comprises an electromagnet.

3. The device as claimed in claim 1, wherein the magnetic portion comprises a permanent magnet.

4. The device as claimed in claim 3, wherein the permanent magnet is made of a neodymium-iron boron composition.

5. The device as claimed in claim 4, wherein the neodymium-iron boron composition has a chemical formula of $Nd_2Fe_{14}B$, has a material grade of N40 and a material residual flux density of about 1.28 Tesla.

6. The device as claimed in claim 1, wherein the second metal portion is integrally, detachably or releasably coupled to the magnetic portion, and wherein the magnetic portion is integrally, detachably or releasably coupled to the first metal portion.

7. The device as claimed in claim 1, further comprising a head integrally, detachably or releasably coupled to the second end of the first metal portion.

8. The device as claimed in claim 7, wherein the head has a length or diameter ranging from about 0.2 to 4 inches.

9. The device as claimed in claim 1, wherein the second metal portion occupies a first volume and the magnetic portion occupies a second volume, and wherein the first volume is less than the second volume.

10. The device as claimed in claim 1, wherein the magnetic portion has a round shape, an oval shape or a shape with at least three sides;
    a diameter or width ranging from about 0.5 inch to 6 inches; and
    a thickness or height ranging from about 0.5 inch to about 6 inches.

11. The device of claim 1, wherein
    the first metal portion has a length ranging from about 1 inch to about 8 inches; and
    the second end of the first metal portion is a ball, a flat disk, or a cylindrical rod,
    wherein the second end of the first metal portion is adapted to match the contours of the patient's body, and has a width or length or diameter ranging from about 0.2 to 4 inches.

12. The device of claim 1, wherein the second metal portion has a round or oval shape or a shape with at least three sides, a diameter or width ranging from about 0.5 inch to 6 inches, and a thickness or height ranging from about 0.5 inch to about 6 inches.

13. The device of claim 1, wherein the first metal portion has a predetermined length according to a severity of the disease or disorder.

* * * * *

UNITED STATES PATENT AND TRADEMARK OFFICE
CERTIFICATE OF CORRECTION

PATENT NO. : 10,625,092 B2
APPLICATION NO. : 15/939317
DATED : April 21, 2020
INVENTOR(S) : Yvonne Ya-Wen Feng Page 1 of 1

It is certified that error appears in the above-identified patent and that said Letters Patent is hereby corrected as shown below:

In the Claims

Column 23, Line 6, In Claim 1, "massage or inch by inch press" should be changed to
-- non-invasive --

Column 23, Line 16, In Claim 1, after "wherein the second side of the second metal portion" insert
-- is flat and even and --

Column 23, Line 17, In Claim 1, after "coupled to the first side of the magnetic portion" insert
-- wherein the first side of the magnetic portion is flat and even --

Signed and Sealed this
Sixth Day of October, 2020

Andrei Iancu
*Director of the United States Patent and Trademark Office*